US012559497B2

(12) United States Patent
Le et al.

(10) Patent No.: US 12,559,497 B2
(45) Date of Patent: Feb. 24, 2026

(54) IMIDAZOPIPERAZINE INHIBITORS OF TRANSCRIPTION ACTIVATING PROTEINS

(71) Applicant: Board of Regents, The University of Texas System, Austin, TX (US)

(72) Inventors: Kang Le, Sugar Land, TX (US); Michael J. Soth, Sugar Land, TX (US); Philip Jones, Houston, TX (US); Jason Bryant Cross, Pearland, TX (US); Timothy Joseph Mcafoos, Pearland, TX (US)

(73) Assignee: Board of Regents, The University of Texas System, Austin, TX (US)

(*) Notice: Subject to any disclaimer, the term of this patent is extended or adjusted under 35 U.S.C. 154(b) by 457 days.

(21) Appl. No.: 18/182,620

(22) Filed: Mar. 13, 2023

(65) Prior Publication Data

US 2023/0312588 A1 Oct. 5, 2023

Related U.S. Application Data

(63) Continuation of application No. PCT/US2021/052898, filed on Sep. 30, 2021.

(60) Provisional application No. 63/086,728, filed on Oct. 2, 2020.

(51) Int. Cl.

| | |
|---|---|
| ***C07D 487/04*** | (2006.01) |
| ***A61K 45/06*** | (2006.01) |
| ***A61P 35/00*** | (2006.01) |

(52) U.S. Cl.

CPC ............ *C07D 487/04* (2013.01); *A61K 45/06* (2013.01); *A61P 35/00* (2018.01)

(58) Field of Classification Search

CPC .................................................... C07D 487/04

See application file for complete search history.

(56) References Cited

U.S. PATENT DOCUMENTS

| | | | |
|---|---|---|---|
| 7,732,603 | B2 | 6/2010 | Mc kenna |
| 8,772,279 | B2 | 7/2014 | Mirizzi |
| 9,145,418 | B2 | 9/2015 | Casuscelli |
| 9,695,176 | B2 | 7/2017 | Degnan |
| 10,899,769 | B2 | 1/2021 | Le |
| 11,058,688 | B2 | 7/2021 | Le |
| 12,186,324 | B2 | 1/2025 | Le |

(Continued)

FOREIGN PATENT DOCUMENTS

| | | |
|---|---|---|
| CN | 103087067 | 5/2013 |
| WO | 2008078291 | 7/2008 |

(Continued)

OTHER PUBLICATIONS

Belikov, V., "A link between chemical structure, properties of substances and their effect on organism", Pharmaceutical Chemistry, Ch. 2.6, Moscow, MEDpress-inform Publishing House, p. 27-9, (2007).

(Continued)

*Primary Examiner* — Andrew D Kosar
*Assistant Examiner* — John D Mcanany
(74) *Attorney, Agent, or Firm* — Cynthia Hathaway; Michael Sertic

(57) ABSTRACT

The present disclosure relates to heterocyclic compounds and methods which may be useful as inhibitors of transcription activating proteins such as CBP and P300 for the treatment or prevention of diseases such as proliferative diseases, inflammatory disorders, autoimmune diseases, and fibrotic diseases.

19 Claims, 1 Drawing Sheet

(56) References Cited

U.S. PATENT DOCUMENTS

| | | | |
|---|---|---|---|
| 2007/0004736 A1 | 1/2007 | Kubo |
| 2009/0149450 A1 | 6/2009 | Beckett |
| 2010/0093740 A1 | 4/2010 | Aissaoui |
| 2010/0240641 A1 | 9/2010 | Papillon |
| 2011/0034443 A1 | 2/2011 | Beckett |
| 2011/0190292 A1 | 8/2011 | Dhar |
| 2012/0220766 A1 | 8/2012 | Tang |
| 2016/0113893 A1 | 4/2016 | Mulvany |
| 2019/0298729 A1 | 10/2019 | Le |
| 2019/0308978 A1 | 10/2019 | Le |
| 2023/0295173 A1 | 9/2023 | Le |
| 2025/0127792 A1 | 4/2025 | Le |

FOREIGN PATENT DOCUMENTS

| | | |
|---|---|---|
| WO | 2008157751 | 12/2008 |
| WO | 2009065298 | 5/2009 |
| WO | 2009082881 | 7/2009 |
| WO | 2009156951 | 12/2009 |
| WO | 2012019427 | 2/2012 |
| WO | 2014199171 | 12/2014 |
| WO | 2016055028 | 4/2016 |
| WO | 2016086200 | 6/2016 |
| WO | 2016113273 | 7/2016 |
| WO | 2016170323 | 10/2016 |
| WO | 2016170324 | 10/2016 |
| WO | 2017184462 | 10/2017 |
| WO | 2017205536 | 11/2017 |
| WO | 2017205538 | 11/2017 |
| WO | 2019191667 | 10/2019 |
| WO | 2019195846 | 10/2019 |
| WO | 2022072647 | 4/2022 |
| WO | 2022072648 | 4/2022 |

OTHER PUBLICATIONS

Bouchal, J. et al., "Transcriptional coactivators p300 and CBP stimulate estrogen receptor-beta signaling and regulate cellular events in prostate cancer", Prostate, 71(4):431-7, (2011).

Bronner, S. et al., "A Unique Approach to Design Potent and Selective Cyclic Adenosine Monophosphate Response Element Binding Protein (CBP) Inhibitors", J Med Chem., 60(24):10151-71, (2017).

CA Registry No. 1069782-59-7 entered into the CA Registry File on Nov. 2, 2008 supplied by ChemBridge Corporation. (Year: 2008).

Cancer [online], Retrieved from the Internet, URL: http://www.nlm.nih.gov/medlineplus/cancer.html on Jul. 6, 2007; (2007).

ChemBridge Product Guide, 2 pages, retrieved from the internet at http://www.chembridge.com/screening_libraries/ on Aug. 9, 2015. (Year: 2015).

Conery, A. et al., "Bromodomain inhibition of the transcriptional coactivators CBP/EP300 as a therapeutic strategy to target the IRF4 network in multiple myeloma", Elife, 5:e10483, 17 pages, (2016).

Crawford, T. et al., "Discovery of a Potent and Selective in Vivo Probe (GNE-272) for the Bromodomains of CBP/EP300", J Med Chem., 59(23):10549-63, (2016).

Database PubChem [online]: "3-[3-cyclopentyl-1-(4-methoxyphenyl)-6,8-dihydro-5H-imidazo[1,5-a]pyrazine-7-carbonyl]-1-methylquinolin-4-one", Database accession No. 26223485, (2009).

Database PubChem [online]: "3-Methyl-7-(2-methylpropanoyl)-6,8-dihydr o-5H-imidazo [I,5-a]pyrazine-1-carbaldehyde", Database accession No. 115267846, (2016).

Database PubChem [online]: "3-Methyl-7-propanoyl-6,8-dihydro-5H-imida zo[I,5-a]pyrazine-1-carbaldehyde", Database accession No. 115267844, (2016).

Database PubChem [online]: "7-Acetyl-6,8-dihydro-5H-imidazo[I,5-a]pyr azine-1-carboxylic acid", Database accession No. 83834364, (2014).

Database PubChem [online]: "7-Propanoyl-6,8-dihydro-5H-imidazo[I,5-a] pyrazine-I-carbaldehyde", Database accession No. 115267864, (2016).

Dörwald, F., "Side Reactions in Organic Synthesis: A Guide to Successful Sysnthesis Design", Wiley: VCH, Weinheim, pp. Preface IX, 1-16, 40-41, 278-309, (2005).

Gatla, H. et al., "Epigenetic regulation of interleukin-8 expression by class I HDAC and CBP in ovarian cancer cells", Oncotarget, 8(41):70798-810, (2017).

Geldenhuys, W. et al., "Virtual Screening to Identify Novel Antagonists for the G Protein-Coupled NK3 Receptor", J Med Chem., 53(22):8080-8, (2010).

Giotopoulos, G. et al., "The epigenetic regulators CBP and p300 facilitate leukemogenesis and represent therapeutic targets in acute myeloid leukemia", Oncogene, 35(3):279-89, (2016).

Golub, T. et al., "Molecular Classification of Cancer: Class Discovery and Class Prediction by Gene Expression Monitoring", Science, 286(5439):531-7, (1999).

International Application No. PCT/US2019/022727; International Search Report and Written Opinion of the International Searching Authority, date of mailing May 14, 2019; 8 pages.

International Application No. PCT/US2019/024976; International Preliminary Report on Patentability, date of issuance Oct. 8, 2020; 7 pages.

International Application No. PCT/US2019/024976; International Search Report and Written Opinion of the International Searching Authority, date of mailing Jul. 22, 2019; 11 pages.

International Application No. PCT/US2019/026379; International Preliminary Report on Patentability, date of issuance Oct. 15, 2020; 6 pages.

International Application No. PCT/US2019/026379; International Search Report and Written Opinion of the International Searching Authority, date of mailing Jul. 30, 2019; 8 pages.

International Application No. PCT/US2021/052897; International Preliminary Report on Patentability, date of issuance Apr. 13, 2023; 5 pages.

International Application No. PCT/US2021/052897; International Search Report and Written Opinion of the International Searching Authority, date of mailing Dec. 28, 2021; 7 pages.

Kharkevich, D., "GEOTAR-Media", Pharmacology, 10th ed., Moscow, Publishing House, p. 73-4, (2010).

Lai, K. et al., "Design and Synthesis of a Biaryl Series as Inhibitors for the Bromodomains of CBP/P300", Bioorg Med Chem Lett., 28(1):15-23, (2018).

Lala, P. et al., "Role of Nitric Oxide in Tumor Progression: Lessons From Experimental Tumors", Cancer Metastasis Rev., 17(1):91-106, (1998).

Machine Translation for CN 103087067 (May 8, 2013). (Year: 2013).

Mashkovskii, M., "Novaya Volna", Medicinal Agents, Moscow, Publishing House, 1:11, (2001).

Mulvihill, M. et al., "Discovery of OSI-906: a selective and orally efficacious dual inhibitor of the IGF-1 receptor and insulin receptor", Future Med Chem., 1(6):1153-71, (2009).

Ogiwara, H. et al., "Targeting p300 Addiction in CBP-Deficient Cancers Causes Synthetic Lethality by Apoptotic Cell Death due to Abrogation of MYC Expression", Cancer Discov., 6(4):430-45, (2016).

Picaud, S. et al., "Generation of a Selective Small Molecule Inhibitor of the CBP/p300 Bromodomain for Leukemia Therapy", Cancer Res., 75(23):5106-19, (2015).

Pokrovskii, V., "Meditsina", Small Medical Encyclopedia, Moscow Publishing House, vol. 5:90-6, (1996).

PubChem CID: 89233298, Compound Summary ZNFWDQVOYHEDS 0-UHFFFAOYSA-N Create Date: Feb. 13, 2015, 8 pages.

Romero, F. et al., "GNE-781, A Highly Advanced Potent and Selective Bromodomain Inhibitor of Cyclic Adenosine Monophosphate Response Element Binding Protein, Binding Protein (CBP)", J Med Chem., 60(22):9162-83, (2017).

Taylor, A.M. et al., "Fragment-Based Discovery of a Selective and Cell-Active Benzodiazepinone CBP/EP300 Bromodomain Inhibitor (CPI-637)", ACS. Med. Chem. Lett., 7:531-6, (2016).

Thornber, C., "Isosterism and Molecular Modification in Drug Design", Chem Soc Rev., 4(8):563-80, (1979).

U.S. Appl. No. 16/370,404; Examiner-Initiated Interview Summary, dated Oct. 28, 2020; 2 pages.

(56) References Cited

OTHER PUBLICATIONS

U.S. Appl. No. 16/370,404; Non-Final Office Action, dated Dec. 12, 2019; 18 pages.
U.S. Appl. No. 16/370,404; Notice of Allowance, dated Feb. 22, 2021; 5 pages.
U.S. Appl. No. 16/370,404; Notice of Allowance, dated Oct. 28, 2020; 6 pages.
U.S. Appl. No. 16/378,309; Non-Final Office Action, dated Jan. 14, 2020; 19 pages.
U.S. Appl. No. 16/378,309; Notice of Allowance, dated Aug. 26, 2020; 7 pages.
U.S. Appl. No. 17/327,217; Corrected Notice of Allowability, dated Dec. 5, 2024; 6 pages.
U.S. Appl. No. 17/327,217; Examiner-Initiated Interview Summary, date of interview Dec. 3, 2024; 1 page.
U.S. Appl. No. 17/327,217; Non-Final Office Action, dated Feb. 12, 2024; 30 pages.
U.S. Appl. No. 17/327,217; Notice of Allowance, dated Aug. 7, 2024; 16 pages.
U.S. Appl. No. 18/182,614; Notice of Allowance, dated Aug. 26, 2025; 8 pages.
Venkatesh, S. et al., "Role of the Development Scientist in Compound Lead Selection and Optimization", J Pharm Sci., 89(2):145-54, (2000).
Yan, G. et al., "Selective inhibition of p300 HAT blocks cell cycle progression, induces cellular senescence, and inhibits the DNA damage response in melanoma cells", J Invest Dermatol., 133(10):2444-52, (2013).
Yang, H. et al., "Small-molecule inhibitors of acetyltransferase p300 identified by high-throughput screening are potent anticancer agents", Mol Cancer Ther., 12(5):610-20, (2013).
Zhulenko, V. et al., "KolosS", Pharmacology, Moscow, Publishing House, p. 34-5, (2008).
International Application No. PCT/US2021/052898; International Preliminary Report on Patentability, date of issuance Apr. 13, 2023; 6 pages.
International Application No. PCT/US2021/052898; International Search Report and Written Opinion of the International Searching Authority, date of mailing Dec. 28, 2021; 8 pages.

(a)
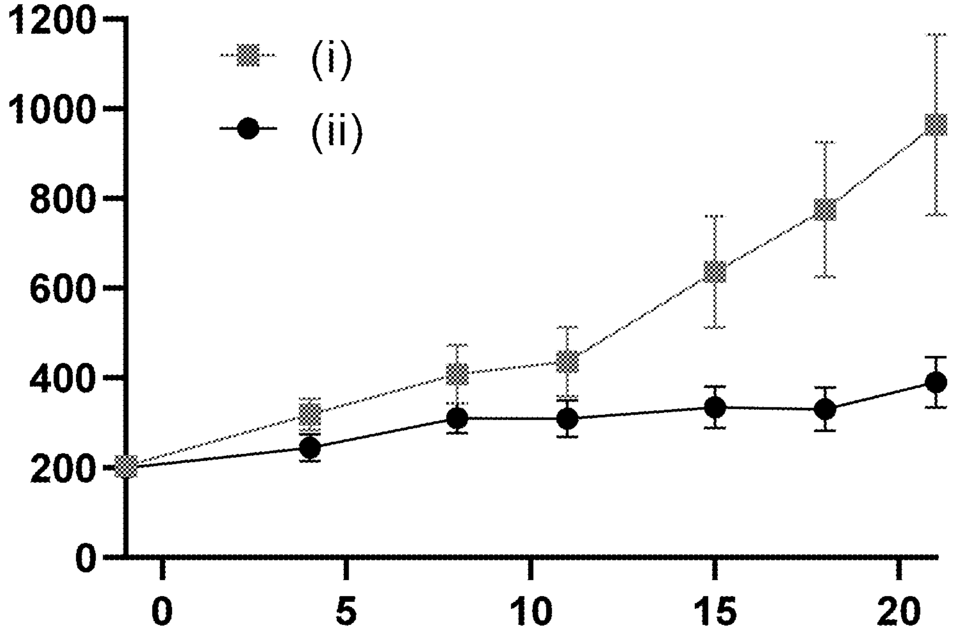
(b)
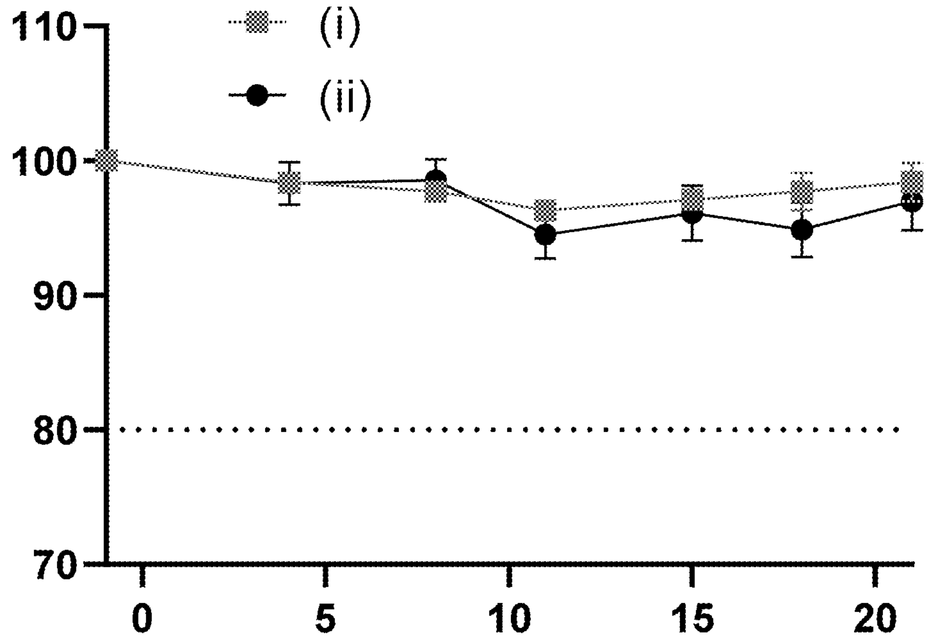

IMIDAZOPIPERAZINE INHIBITORS OF TRANSCRIPTION ACTIVATING PROTEINS

This application is a bypass continuation of International Application No. PCT/US2021/052898, filed Sep. 30, 2021, which claims the benefit of priority to U.S. Provisional Application No. 63/086,728, filed Oct. 2, 2020, the disclosures of each are hereby incorporated by reference as if written herein in their entireties.

Disclosed herein are new imidazopiperazine compounds and compositions and their application as pharmaceuticals for the treatment of disease. Methods of inhibition of the activity of transcription activating proteins such as CBP and P300 in a human or animal subject are also provided for the treatment of diseases such as cancer.

Chromatin is a combination of DNA and protein, found in eukaryotic nuclei, that makes up chromosomes. Chromatin can be classified as either heterochromatin (condensed) and euchromatin (extended) forms. The major protein components of chromatin are termed histones, which serve as scaffolds on which DNA is packaged and compacted into a smaller volume to fit in the nucleus. Histones are implicated in the processes of mitosis and meiosis, and are thought to play important roles in the expression and replication of DNA. Importantly, histones undergo post-translational modification ("PTM") at various amino acid sites, which modulates chromatin structure and thereby affects transcription. This modification provides a mechanism for "epigenetics", or the control of gene activity and expression that does not arise from the direct alteration of the DNA sequence.

Acetylation of lysine residues is a PTM with broad relevance to cellular signaling and disease biology. Lysine acetylation, which is particularly abundant in nuclear macromolecular complexes, plays a key role in chromatin regulation and transcriptional control. In cells, the principal 'readers' of the acetyl-lysine marks are the bromodomains (BRDs), which are a diverse family of evolutionary conserved protein-protein interaction modules that specifically recognize and bind to acetylated lysine residues. The bromodomains, together with the enzymes that 'write' (Histone acetyl transferases, HATs) and 'erase' (histone deacetylases, HDACs) acetylated lysine residues on histone and non-histone proteins, critically control the regulation of gene expression and thereby cell phenotype including proliferation, cell differentiation and metabolism. Besides chromatin, many other proteins are also post-translationally modified such as p53, which could also be potentially recognized by bromodomain proteins. Because chromatin-mediated processes are often deregulated in cancer, targeting epigenetic reader proteins like BET (dual-BRD4 containing proteins), CREBBP, ATAD2A, SMARCA2/4 and Tripartite Motif-containing 24 (TRIM24) represent promising targets for drug discovery. As illustrated by the development of selective inhibitors of the BET family of bromodomains, the conserved BRD fold represents a promising pocket for the development of small pharmaceutically active molecules.

The histone acetyltransferase paralogues, cyclic adenosine monophosphate response element binding protein, binding protein (CBP, CREBBP, or CREB-binding protein) and adenoviral E1A binding protein of 300 kDa (P300 or EP300), are highly homologous and are two closely related multi-domain transcription activating proteins containing both a histone acetyl transferase (HAT) as well as a bromodomain, and have important roles in histone acetylation. They are key transcriptional co-activators that are essential for a multitude of cellular processes, and have also been implicated in several human pathological conditions, including cancer.

CBP and P300 bind to chromatin via their bromodomains, and once associated with chromatin, this complex recruits additional transcriptional machinery to modulate gene expression leading to the recruitment of various transcriptional proteins to modulate gene expression. In addition to chromatin, CBP/P300 have been shown to bind non-histone proteins; for instance, CBP has been described to recognize acetylated p53 at K382 following DNA damage. Several studies have implicated CBP/P300 in the development, maintenance, and/or progression of cancer and tumor immunity, and therefore CBP/P300 inhibitors are the target of current efforts to develop anti-cancer agents. In particular, CBP has been found to regulate expression of MYC, a transcription factor and oncogene widely up-regulated in many human cancers, which suggests a potential therapeutic strategy for targeting multiple myeloma and other lymphoid malignancies, and solid tumors.

In addition, CBP and P300 are known co-activators of the androgen receptor (AR), and have been implicated in enhancing the response to androgen. Consistent with this, CBP/P300 have been proposed to play an oncogenic role in prostate cancer, and up-regulation of both proteins has been observed in tumors. CBP inhibitors selectively inhibit proliferation in lineage-specific tumour types, including several hematological malignancies and androgen receptor-positive prostate cancer. CBP inhibitors inhibit the androgen receptor transcriptional program in both androgen-sensitive and castration-resistant prostate cancer and inhibit tumour growth in prostate cancer xenograft models.

CBP also has relevance to cancer immunotherapy, and the ability of CBP bromodomain inhibitors to impair Treg differentiation and suppressive function has been described. This activity could constitute a novel small molecule approach to enhance the response to cancer immunotherapy.

Compounds and pharmaceutical compositions, certain of which have been found to bind to and inhibit interactions of CBP and P300 have been discovered, together with methods of synthesizing and using the compounds including methods for the treatment of CBP- and P300-mediated diseases in a patient by administering the compounds.

BRIEF DESCRIPTION OF THE DRAWINGS

FIG. 1 shows (a) change in tumor volume (vertical axis, $mm^3$) over time (horizontal axis, days) and (b) % change in body weight upon treatment of DOHH2 xenografts by (i) vehicle, and (ii) the Example 1 compound.

DETAILED DESCRIPTION

Provided herein is a compound having structural Formula I:

(I)

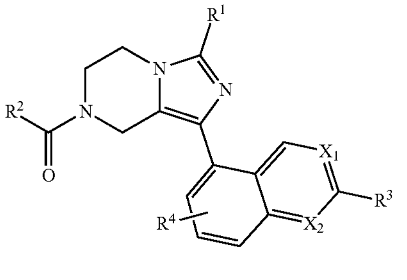

or a salt thereof, wherein:

$X_1$ is N and $X_2$ is CH;

$R^1$ is chosen from cyclopropyl, tetrahydro-2H-pyran-4-yl, and 2-oxabicyclo[2.2.2]octan-4-yl, any of which is optionally substituted with 1 or 2 $R^5$ groups;

$R^2$ is methyl;

$R^3$ is chosen from pyridin-3-yl and thiazol-5-yl, and is optionally substituted with 1 or 2 $R^7$ groups;

$R^4$ is chosen from H and fluoro;

each $R^5$ is independently chosen from alkyl, alkoxy, cyano, carboxy, halo, haloalkyl, haloalkoxyl, hydroxy, and oxo;

each occurrence of $R^7$ is independently chosen from —C(O)$NR^8R^9$ and alkyl, and $R^8$ and $R^9$ are independently chosen from hydrogen and alkyl.

Certain compounds disclosed herein may possess useful inhibiting activity for CBP or P300, and may be used in the treatment or prophylaxis of a disease or condition in which CBP or P300 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting CBP or P300. Other embodiments provide methods for treating a disorder mediated by CBP or P300 in a patient in need of such treatment, comprising administering to said patient a therapeutically effective amount of a compound or composition according to the present disclosure. Also provided is the use of certain compounds disclosed herein for use in the manufacture of a medicament for the treatment of a disease or condition ameliorated by the inhibition of CBP and P300.

In certain embodiments, $R^1$ is chosen from cyclopropyl, tetrahydro-2H-pyran-4-yl, 2-oxabicyclo[2.2.2]octan-4-yl.

In certain embodiments, $R^3$ is chosen from pyridin-3-yl and thiazol-5-yl, and is optionally substituted with 1 or 2 $R^7$ groups. In certain embodiments, $R^3$ is chosen from pyridin-3-yl and thiazol-5-yl, and is optionally substituted with 1 $R^7$ group. In certain embodiments, $R^3$ is chosen from 6-(methylcarbamoyl)pyridin-3-yl, 2-methylthiazol-5-yl, 2,4-dimethylthiazol-5-yl, 6-methylpyridin-3-yl, and 2-(methylcarbamoyl) thiazol-5-yl. In certain embodiments, $R^3$ is chosen from:

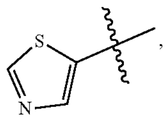
,
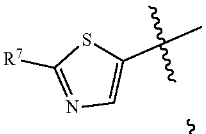
,
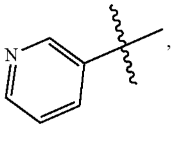
, and
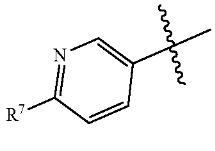
.

In certain embodiments, $R^3$ is

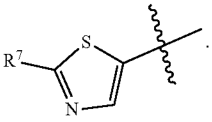
.

Also provided herein is a compound having structural Formula I:

(I)

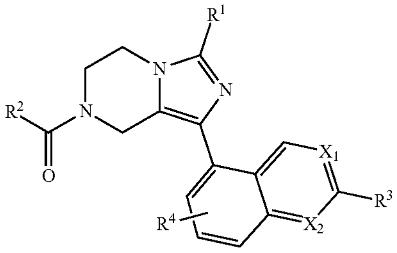

or a salt thereof, wherein:

$X_1$ is N and $X_2$ is CH;

$R^1$ is tetrahydro-2H-pyran-4-yl optionally substituted with 1 or 2 $R^5$ groups;

$R^2$ is methyl;

$R^3$ is thiazol-5-yl optionally substituted with 1 or 2 $R^7$ groups;

$R^4$ is chosen from H and fluoro;

each $R^5$ is independently chosen from alkyl, alkoxy, cyano, carboxy, halo, haloalkyl, haloalkoxyl, hydroxy, and oxo;

each occurrence of $R^7$ is independently chosen from —C(O)$NR^8R^9$ and alkyl, and $R^8$ and $R^9$ are independently chosen from hydrogen and alkyl.

Also provided herein is a compound having structural Formula II:

(II)

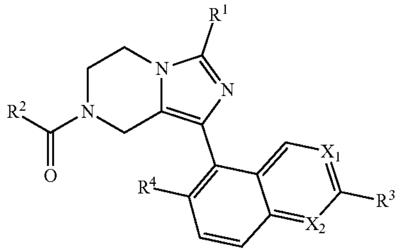

or a salt thereof, wherein:

$X_1$ is N and $X_2$ is CH;

$R^1$ is tetrahydro-2H-pyran-4-yl optionally substituted with 1 or 2 $R^5$ groups;

$R^2$ is methyl;

$R^3$ is chosen from pyridin-3-yl and thiazol-5-yl, and is optionally substituted with 1 or 2 $R^7$ groups;

$R^4$ is chosen from H or fluoro;

each $R^5$ is independently chosen from alkyl, alkoxy, cyano, carboxy, halo, haloalkyl, haloalkoxyl, hydroxy, and oxo;

each occurrence of $R^7$ is independently chosen from —C(O)$NR^8R^9$ and alkyl, and $R^8$ and $R^9$ are independently chosen from hydrogen and alkyl.

In certain embodiments, $R^1$ is tetrahydro-2H-pyran-4-yl.

In certain embodiments, $R^2$ is methyl.

In certain embodiments, $R^3$ is thiazol-5-yl, and is optionally substituted with 1 $R^7$ group. In certain embodiments, $R^3$ is chosen from 2-methylthiazol-5-yl, 2,4-dimethylthiazol-5- yl, 6-methylpyridin-3-yl, and 2-(methylcarbamoyl) thiazol-5-yl. In certain embodiments, $R^3$ is chosen from:

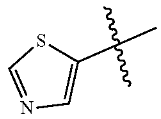
and
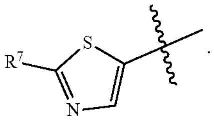

In certain embodiments, $R^3$ is

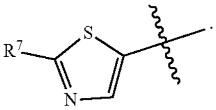

In certain embodiments, $R^7$ is —C(O)NR$^8$R$^9$. In certain further embodiments, $R^7$ is —C(O)NHCH$_3$.

In certain embodiments, $R^7$ is $C_{1-6}$alkyl, In certain further embodiments, $R^7$ is methyl.

In certain embodiments, $R^8$ and $R^9$ are independently chosen from hydrogen and $C_{1-6}$ alkyl. In certain further embodiments, $R^8$ and $R^9$ are independently chosen from hydrogen and methyl.

In certain embodiments, at least one of $R^8$ and $R^9$ is hydrogen. In certain embodiments, at most one of $R^8$ and $R^9$ is hydrogen.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

The present disclosure also relates to a method of inhibiting at least one function of CBP comprising the step of contacting CBP with a compound as described herein, or a salt thereof. The cell phenotype, cell proliferation, activity of CBP, change in biochemical output produced by active CBP, expression of CBP, or binding of CBP with a natural binding partner may be monitored. Such methods may be modes of treatment of disease, biological assays, cellular assays, biochemical assays, or the like.

The present disclosure also relates to a method of inhibiting at least one function of P300 comprising the step of contacting P300 with a compound as described herein or a salt thereof. The cell phenotype, cell proliferation, activity of P300, change in biochemical output produced by active P300, expression of P300, or binding of P300 with a natural binding partner may be monitored. Such methods may be modes of treatment of disease, biological assays, cellular assays, biochemical assays, or the like.

Also provided herein is a method of treatment of a CBP-mediated disease comprising the administration of a therapeutically effective amount of a compound as disclosed herein, or a salt thereof, to a patient in need thereof.

Also provided herein is a method of treatment of a P300-mediated disease comprising the administration of a therapeutically effective amount of a compound as disclosed herein, or a salt thereof, to a patient in need thereof.

In certain embodiments, the disease is a proliferative disease.

In certain embodiments, the disease is cancer.

Also provided herein is a compound as disclosed herein, or a salt thereof, for use as a medicament.

Also provided herein is a compound as disclosed herein, or a salt thereof, for use as a medicament for the treatment of a CBP-mediated disease.

Also provided herein is a compound as disclosed herein, or a salt thereof, for use as a medicament for the treatment of a P300-mediated disease.

Also provided is the use of a compound as disclosed herein, or a salt thereof, as a medicament.

Also provided is the use of a compound as disclosed herein, or a salt thereof, as a medicament for the treatment of a CBP-mediated disease.

Also provided is the use of a compound as disclosed herein, or a salt thereof, as a medicament for the treatment of a P300-mediated disease.

Also provided is a compound as disclosed herein, or a salt thereof, for use in the manufacture of a medicament for the treatment of a CBP-mediated disease.

Also provided is a compound as disclosed herein, or a salt thereof, for use in the manufacture of a medicament for the treatment of a P300-mediated disease.

Also provided is the use of a compound as disclosed herein, or a salt thereof, for the treatment of a CBP-mediated disease.

Also provided is the use of a compound as disclosed herein, or a salt thereof, for the treatment of a P300-mediated disease.

Also provided herein is a method of inhibition of CBP comprising contacting CBP with a compound as disclosed herein, or a salt thereof.

Also provided herein is a method of inhibition of P300 comprising contacting P300 with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

In certain embodiments, the CBP-mediated disease is cancer.

In certain embodiments, the P300-mediated disease is cancer.

Also provided is a method of modulation of a CBP-mediated function in a subject comprising the administration of a therapeutically effective amount of a compound as disclosed herein, or a salt thereof.

Also provided is a method of modulation of a P300-mediated function in a subject comprising the administration of a therapeutically effective amount of a compound as disclosed herein, or a salt thereof.

Also provided is a pharmaceutical composition comprising a compound as disclosed herein, or a salt thereof, together with a pharmaceutically acceptable carrier.

In certain embodiments, the pharmaceutical composition is formulated for oral administration.

In certain embodiments, the pharmaceutical composition is formulated for parenteral administration.

In certain embodiments, the oral pharmaceutical composition is chosen from a tablet and a capsule.

Abbreviations and Definitions

As used herein, the terms below have the meanings indicated.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a $—C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy." as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene ($—CH_2—$). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH—$).

The term "amino," as used herein, alone or in combination, refers to —NRR, wherein R and R are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term “arylalkynyl” or “aralkynyl,” as used herein, alone or in combination, refers to an aryl group attached to the parent molecular moiety through an alkynyl group.

The term “arylalkanoyl” or “aralkanoyl” or “aroyl.” as used herein, alone or in combination, refers to an acyl radical derived from an aryl-substituted alkanecarboxylic acid such as benzoyl, napthoyl, phenylacetyl, 3-phenylpropionyl(hydrocinnamoyl), 4-phenylbutyryl, (2-naphthyl) acetyl, 4-chlorohydrocinnamoyl, and the like.

The term aryloxy as used herein, alone or in combination, refers to an aryl group attached to the parent molecular moiety through an oxy.

The terms “benzo” and “benz,” as used herein, alone or in combination, refer to the divalent radical $C_6H_4$=derived from benzene. Examples include benzothiophene and benzimidazole.

The term “carbamate,” as used herein, alone or in combination, refers to an ester of carbamic acid (—NHCOO—) which may be attached to the parent molecular moiety from either the nitrogen or acid end, and which may be optionally substituted as defined herein.

The term “O-carbamyl” as used herein, alone or in combination, refers to a —OC(O)NRR', group— with R and R' as defined herein.

The term “N-carbamyl” as used herein, alone or in combination, refers to a ROC(O)NR'— group, with R and R' as defined herein.

The term “carbonyl,” as used herein, when alone includes formyl [—C(O)H] and in combination is a —C(O)— group.

The term “carboxyl” or “carboxy.” as used herein, refers to —C(O)OH or the corresponding “carboxylate” anion, such as is in a carboxylic acid salt. An “O-carboxy” group refers to a RC(O)O— group, where R is as defined herein. A “C-carboxy” group refers to a —C(O)OR groups where R is as defined herein.

The term “cyano,” as used herein, alone or in combination, refers to —CN.

The term “cycloalkyl.” or, alternatively, “carbocycle,” as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. “Bicyclic” and “tricyclic” as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term “ester.” as used herein, alone or in combination, refers to a carboxy group bridging two moieties linked at carbon atoms.

The term “ether.” as used herein, alone or in combination, refers to an oxy group bridging two moieties linked at carbon atoms.

The term “halo,” or “halogen,” as used herein, alone or in combination, refers to fluorine, chlorine, bromine, or iodine.

The term “haloalkoxy,” as used herein, alone or in combination, refers to a haloalkyl group attached to the parent molecular moiety through an oxygen atom.

The term “haloalkyl,” as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. “Haloalkylene” refers to a haloalkyl group attached at two or more positions. Examples include fluoromethylene (—CFH—), difluoromethylene ($—CF_2—$), chloromethylene (—CHCl—) and the like.

The term “heteroalkyl,” as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, $—CH_2—NH—OCH_3$.

The term “heteroaryl”, as used herein, alone or in combination, refers to a 3 to 15 membered unsaturated heteromonocyclic ring, or a fused monocyclic, bicyclic, or tricyclic ring system in which all of the fused rings are aromatic, which contains at least one atom chosen from N, O, and S. The term “heteroaryl” thus encompasses, for example, pyridine, thiophene, quinoline, and phenanthridine. The term “heteroaryl” thus does not encompass, for example, indoline, and 2,3-dihydrobenzofuran. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, and wherein heteroaryl rings are fused with other heteroaryl rings. Examples of heteroaryl groups include pyrrolyl, pyrrolinyl, imidazolyl, pyrazolyl, pyridyl, pyrimidinyl, pyrazinyl, pyridazinyl, triazolyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, and the like. Exemplary tricyclic heterocyclic groups include carbazolyl, phenanthrolinyl, dibenzofuranyl, acridinyl, phenanthridinyl, and the like.

The terms “heterocycloalkyl” and, interchangeably, “heterocycle,” as used herein, alone or in combination, each refer to a saturated, partially unsaturated, or fully unsaturated (but not fully aromatic) monocyclic, bicyclic, or tricyclic heterocyclic group containing at least one heteroatom as a ring member, wherein each said heteroatom may be independently chosen from nitrogen, oxygen, and sulfur. The term “heterocycloalkyl” thus excludes fully aromatic ring systems such as pyridine, pyrimidine, quinoline, and acridine. The term “heterocycloalkyl” thus includes partially aromatic bicyclic and larger ring systems such as 1,2,3,4-tetrahydroquinoline, 5,6,7,8-tetrahydroquinoline, and indoline. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro [1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

Certain compounds in the present disclosure can comprise diazanaphthalene groups, which will be understood as derivatives of naphthalene in which two of the non-bridgehead CH groups is replaced with N. The term "diazanaphthalene" encompasses the four isomers of benzodiazine, which have both nitrogens in the same ring, and the six isomers of naphthyridine, which have nitrogens on different rings.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR, wherein R and R are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to $—NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the $—SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to $—S(O)_2—$.

The term "N-sulfonamido" refers to a $RS(=O)_2NR'—$ group with R and R' as defined herein.

The term "S-sulfonamido" refers to a $—S(=O)_2NRR'$, group, with R and R' as defined herein.

The terms "thia" and "thio," as used herein, alone or in combination, refer to a —S—group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl-C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R'as defined herein.

The term "thiocyanato" refers to a —CNS group.

The term "trihalomethanesulfonamido" refers to a $X_3CS(O)_2NR—$ group with X is a halogen and R as defined herein.

The term "trihalomethanesulfonyl" refers to a $X_3CS(O)_2—$ group where X is a halogen.

The term "trihalomethoxy" refers to a $X_3CO—$ group where X is a halogen.

The term "trisubstituted silyl." as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., $-CH_2CH_3$), fully substituted (e.g., $-CF_2CF_3$), monosubstituted (e.g., $-CH_2CH_2F$) or substituted at a level anywhere in-between fully substituted and monosubstituted (e.g., $-CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3 . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as $-C(O)N(R)-$ may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome." and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"CBP inhibitor", as used herein, refers to a compound that binds to and inhibits the bromodomain of CBP with measurable affinity and activity. In certain embodiments, a CBP inhibitor exhibits an IC50 with respect to CBP activity of no more than about 100 μM and more typically not more than about 50 μM, as measured in the CBP (assay name) described generally herein. "IC50" is that concentration of inhibitor which reduces the activity of the bromodomain of CBP to half-maximal level. Certain compounds disclosed herein have been discovered to exhibit inhibition against CBP. In certain embodiments, compounds will exhibit an IC50 with respect to CBP of no more than about 20 μM; in further embodiments, compounds will exhibit an IC50 with respect to CBP of no more than about 5 μM; in yet further embodiments, compounds will exhibit an IC50 with respect to CBP of not more than about 200 nM; in yet further embodiments, compounds will exhibit an IC50 with respect to CBP of not more than about 50 nM; in yet further embodiments, compounds will exhibit an IC50 with respect to CBP of not more than about 10 nM; in yet further embodiments, compounds will exhibit an IC50 with respect to CBP of not more than about 2 nM, as measured in the CBP assay described herein.

"P300 inhibitor", as used herein, refers to a compound that binds to and inhibits the bromodomain of P300 with measurable affinity and activity. In certain embodiments, a P300 inhibitor exhibits an IC50 with respect to P300 activity of no more than about 100 μM and more typically not more than about 50 μM, as measured in the P300 (assay name) described generally herein. "IC50" is that concentration of inhibitor which reduces the activity of the bromodomain of P300 to half-maximal level. Certain compounds disclosed herein have been discovered to exhibit inhibition against P300. In certain embodiments, compounds will exhibit an IC50 with respect to P300 of no more than about 20 μM; in further embodiments, compounds will exhibit an IC50 with respect to P300 of no more than about 5 μM; in yet further embodiments, compounds will exhibit an IC50 with respect to P300 of not more than about 200 nM; in yet further embodiments, compounds will exhibit an IC50 with respect to P300 of not more than about 50 nM; in yet further embodiments, compounds will exhibit an IC50 with respect to P300 of not more than about 10 nM; in yet further embodiments, compounds will exhibit an IC50 with respect to P300 of not more than about 2 nM, as measured in the P300 assay described herein.

In some embodiments, certain compounds disclosed herein interfere with the associating of CBP and/or EP300 with histones, in particular acetylated lysines in histones. In some embodiments, certain compounds disclosed herein inhibit binding of CBP and/or EP300 to chromatin (e.g., histone associated DNA). In some embodiments, certain compounds disclosed herein inhibit and/or reduces binding of the CBP bromodomain and/or EP300 bromodomain to chromatin (e.g., histone associated DNA). In some embodiments, certain compounds disclosed herein do not affect association of other domains of CBP and/or EP300 to chromatin. In some embodiments, certain compounds disclosed herein bind to the CBP and/or EP300 primarily (e.g., solely) through contacts and/or interactions with the CBP bromodomain and/or EP300 bromodomain. In some embodiments, certain compounds disclosed herein bind to the CBP and/or EP300 through contacts and/or interactions with the CBP bromodomain and/or EP300 bromodomain as well as additional CBP and/or EP300 residues and/or domains. Methods of assaying association with chromatin are known in the art and include, but are not limited to, chromatin fractionation, BRET assay (Promega), FRAP assay, Chromatin Immunoprecipitation (ChIP), biophysical binding assay, and/or Histone Association Assay. Sec, e.g., Das et al., BioTechniques 37:961-969 (2004).

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, 2,2,2-trifluoroacetate=trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Oral Administration

The compounds of the present disclosure may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules, solutions or suspensions in an aqueous liquid or a non-aqueous liquid, or as an oil-in-water liquid emulsion or a water-in-oil liquid emulsion. The active ingredient may also be presented as a bolus, electuary or paste.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Parenteral Administration

Compounds of the present disclosure may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example scaled ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions. Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example scaled ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present disclosure may be administered topically (for example to the skin, mucous membranes, car, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Certain compounds disclosed herein may be administered topically, that is by non-systemic administration. This includes the application of a compound disclosed herein externally to the epidermis or the buccal cavity and the instillation of such a compound into the car, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Rectal, Buccal, and Sublingual Administration

Suppositories for rectal administration of the compounds of the present disclosure can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Administration by Inhalation

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the disclosure may be prepared by any of the well-known techniques of pharmacy, such as effective formulation and administration procedures. Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Combinations and Combination Therapy

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with anti-cancer (chemotherapeutic) drugs. Classes of anti-cancer drugs include, but are not limited to: alkylating agents, anti-metabolites, antimitotics, checkpoint inhibitors, plant alkaloids and terpenoids, topoisomerase inhibitors, cytotoxic antibiotics, aromatase inhibitors, angiogenesis inhibitors, anti-steroids and anti-androgens, mTOR inhibitors, tyrosine kinase inhibitors, and others.

For use in cancer and neoplastic diseases a CBP/EP300 inhibitor may be optimally used together with one or more of the following non-limiting examples of anti-cancer agents:

(1) alkylating agents, including but not limited to carmustine, chlorambucil (LEUKERAN), cisplatin (PLATIN), carboplatin (PARAPLATIN), oxaliplatin (ELOXATIN), streptozocin (ZANOSAR), busulfan (MYLERAN), dacarbazine, ifosfamide, lomustine (CCNU), melphalan (ALKERAN), procarbazine (MATULAN), temozolomide (TEMODAR), thiotepa, and cyclophosphamide (ENDOXAN);

(2) anti-metabolites, including but not limited to cladribine (LEUSTATIN), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), raltitrexed;

(3) antimitotics, which are often plant alkaloids and terpenoids, or derivatives thereof, including but not limited to taxanes such as docetaxel (TAXITERE) and paclitaxel (ABRAXANE, TAXOL); *vinca* alkaloids such as vincristine (ONCOVIN), vinblastine, vindesine, and vinorelbine (NAVELBINE);

(4) checkpoint inhibitors, such as anti-PD-1 or PD-L1 antibodies pembrolizumab (KEYTRUDA), nivolumab (OPDIVO), MEDI4736, and MPDL3280A; anti-CTLA-4 antibody ipilimumab (YERVOY); and those that target LAG3 (lymphocyte activation gene 3 protein), KIR (killer cell immunoglobulin-like receptor), 4-1BB (tumour necrosis factor receptor superfamily member 9), TIM3 (T-cell immunoglobulin and mucin-domain containing-3) and OX40 (tumour necrosis factor receptor superfamily member 4);

(5) topoisomerase inhibitors, including but not limited to camptothecin (CTP), irinotecan (CAMPTOSAR), topotecan (HYCAMTIN), teniposide (VUMON), and etoposide (EPOSIN);

(6) cytotoxic antibiotics, including but not limited to actinomycin D (dactinomycin, COSMEGEN), bleomycin (BLENOXANE) doxorubicin (ADRIAMYCIN), daunorubicin (CERUBIDINE), epirubicin (ELLENCE), fludarabine (FLUDARA), idarubicin, mitomycin (MITOSOL), mitoxantrone (NOVANTRONE), plicamycin;

(7) aromatase inhibitors, including but not limited to aminoglutethimide, anastrozole (ARIMIDEX), letrozole (FEMARA), vorozole (RIVIZOR), exemestane (AROMASIN);

(8) angiogenesis inhibitors, including but not limited to genistein, sunitinib (SUTENT) and bevacizumab (AVASTIN);

(9) anti-steroids and anti-androgens such as aminoglutethimide (CYTADREN), bicalutamide (CASODEX), cyproterone, flutamide (EULEXIN), nilutamide (NILANDRON);

(10) tyrosine kinase inhibitors, including but not limited to imatinib (GLEEVEC), erlotinib (TARCEVA), lapatininb (TYKERB), sorafenib (NEXAVAR), and axitinib (INLYTA);

(11) mTOR inhibitors such as everolimus, temsirolimus (TORISEL), and sirolimus;

(12) monoclonal antibodies such as trastuzumab (HERCEPTIN) and rituximab (RITUXAN);

(13) other agents, such as amsacrine; *Bacillus* Calmette-Guérin (B—C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon;

leucovorin; leuprolide (LUPRON); levamisole; lonidamine; mesna; metformin; mitotane (o.p'-DDD, LYSODREN); nocodazole; octreotide (SANDOSTATIN); perifosine;

porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

Where a subject is suffering from or at risk of suffering from an inflammatory condition, a CBP/EP300 inhibitor compound described herein is optionally used together with one or more agents or methods for treating an inflammatory condition in any combination. Therapeutic agents/treatments for treating an autoimmune and/or inflammatory condition include, but are not limited to any of the following examples:

(1) corticosteroids, including but not limited to cortisone, dexamethasone, and methylprednisolone;
(2) nonsteroidal anti-inflammatory drugs (NSAIDs), including but not limited to ibuprofen. naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE);
(3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN);
(4) CD20 blockers, including but not limited to rituximab (RITUXAN);
(5) Tumor Necrosis Factor (TNF) blockers, including but not limited to etanercept (ENBREL), infliximab (REMICADE) and adalimumab (HUMIRA);
(6) interleukin-1 receptor antagonists, including but not limited to anakinra (KINERET);
(7) interleukin-6 inhibitors, including but not limited to tocilizumab (ACTEMRA);
(8) interleukin-17 inhibitors, including but not limited to AIN457;
(9) Janus kinase inhibitors, including but not limited to tasocitinib; and
(10) syk inhibitors, including but not limited to fostamatinib.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating CBP-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of CBP-mediated disorders.

Thus, in another aspect, certain embodiments provide methods for treating P300-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of P300-mediated disorders.

The compounds, compositions, and methods disclosed herein are useful for the treatment of disease. In certain embodiments, the disease is one of dysregulated cellular proliferation, including cancer. The cancer may be hormone-dependent or hormone-resistant, such as in the case of breast cancers. In certain embodiments, the cancer is a solid tumor. In other embodiments, the cancer is a lymphoma or leukemia. In certain embodiments, the cancer is and a drug resistant phenotype of a cancer disclosed herein or known in the art. Tumor invasion, tumor growth, tumor metastasis, and angiogenesis may also be treated using the compositions and methods disclosed herein. Precancerous neoplasias are also treated using the compositions and methods disclosed herein.

Cancers to be treated by the methods disclosed herein include colon cancer, breast cancer, ovarian cancer, lung cancer and prostate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; and thyroid and other endocrine glands. The term "cancer" also encompasses cancers that do not necessarily form solid tumors, including Hodgkin's disease, non-Hodgkin's lymphomas, multiple myeloma and hematopoietic malignancies including leukemias (Chronic Lymphocytic Leukemia (CLL), Acute Lymphocytic Leukemia (ALL), Chronic Myelogenous Leukemia (CML), Acute Myelogenous Leukemia (AML),) and lymphomas including lymphocytic, granulocytic and monocytic. Additional types of cancers which may be treated using the compounds and methods of the invention include, but are not limited to, adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor.

In certain embodiments, the compositions and methods disclosed herein are useful for preventing or reducing tumor invasion and tumor metastasis.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Compound Synthesis

Compounds of the present disclosure can be prepared using methods illustrated in general synthetic schemes and experimental procedures detailed below. General synthetic schemes and experimental procedures are presented for purposes of illustration and are not intended to be limiting. Starting materials used to prepare compounds of the present disclosure are commercially available or can be prepared using routine methods known in the art.

List of Abbreviations $Ac_2O$=acetic anhydride; AcCl=acetyl chloride; AcOH=acetic acid; AIBN=azobisisobutyronitrile; aq.=aqueous; $BPin_2$=bis(pinacolato)diboron=4,4,4',4',5,5,5',5'-octamethyl-2,2'-bi-1,3,2-dioxaborolane; Brettphos=2-(Dicyclohexylphosphino) 3,6-dimethoxy-2',4',6'-triisopropyl-1,1'-biphenyl; $Bu_3SnH$=tributyltin hydride; CBz=carboxybenzyl=$PhCH_2OC(=O)$—; CBzCl=benzyl chloroformate=$PhCH_2OC(=O)Cl$; $CD_3OD$=deuterated methanol; $CDCl_3$=deuterated chloroform; CDI=1,1'-Carbonyldiimidazole; DAST=diethylaminosulfur trifluoride; DBU=1,8-diazabicyclo[5.4.0]undec-7-ene; DCE=1,2-dichloroethane; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=diphenylphosphoryl azide; dppe=1,2-bis(diphenylphosphino) ethane; dppf=1.1'-bis(diphenylphosphino) ferrocene; EDC.HCl=EDCI.HCl=1-ethyl-3-(3-dimethylaminopropyl) carbodiimide hydrochloride; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; iPr=i-Pr=isopropyl=$(CH_3)_2CH$—; i-PrOH=isopropanol=$(CH_3)_2CH$—OH; LAH=$LiAlH_4$=lithium aluminium hydride; LiHMDS=LIN$(TMS)_2$=Lithium bis(trimethylsilyl)amide; MeCN=acetonitrile; MeOH=methanol; MP-carbonate resin=macroporous triethylammonium methylpolystyrene carbonate resin; MsCl=mesyl chloride; MTBE=methyl tertiary butyl ether; MW=microwave irradiation; n-BuLi=n-butyllithium; NaHMDS=Sodium bis(trimethylsilyl)amide; NaOMe=sodium methoxide; NaOtBu=sodium tert-butoxide; NBS=N-bromosuccinimide; NCS=N-chlorosuccinimide; NIS=N-iodosuccinimide; NMP=N-Methyl-2-pyrrolidone; $PdCl_2(dppf)$=$Pd(dppf)Cl_2$=[1,1'-bis (diphenylphosphino) ferrocene]palladium (II) chloride; $Pd(Ph_3)_4$=tetrakis(triphenyl-phosphine) palladium (0); $Pd_2(dba)_3$=tris(dibenzylideneacetone) dipalladium (0); $PdCl_2(PPh_3)_2$=bis(triphenylphosphine) palladium (II) dichloride; PG=protecting group; prep-HPLC=preparative high-performance liquid chromatography; PyBop=(benzotriazol-1-yloxy)-tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; tBu=t-Bu=tert-butyl=$(CH_3)_3C$—; t-BuOH=tert-butanol=$(CH_3)_3C$—OH; T3P=Propylphosphonic Anhydride; TBS=TBDMS=tert-butyldimethylsilyl; TBSCl=TBDMSCl=tert-butyldimethylchlorosilane; TEA=$Et_3N$=triethylamine; TFA=trifluoroacetic acid; TFAA=trifluoroacetic anhydride; THF=tetrahydrofuran; Tol=toluene; TsCl=tosyl chloride; XPhos=2-dicyclohexylphosphino-2',4',6'-triisopropylbiphenyl; Xphos Pd G2=chloro(2-dicyclohexylphosphino-2',4',6'-triisopropyl-1,1'-biphenyl) [2-(2'-amino-1,1'-biphenyl)]palladium (II).

General Synthetic Methods for Preparing Compounds

The following schemes can be used to practice the present disclosure.

Scheme I

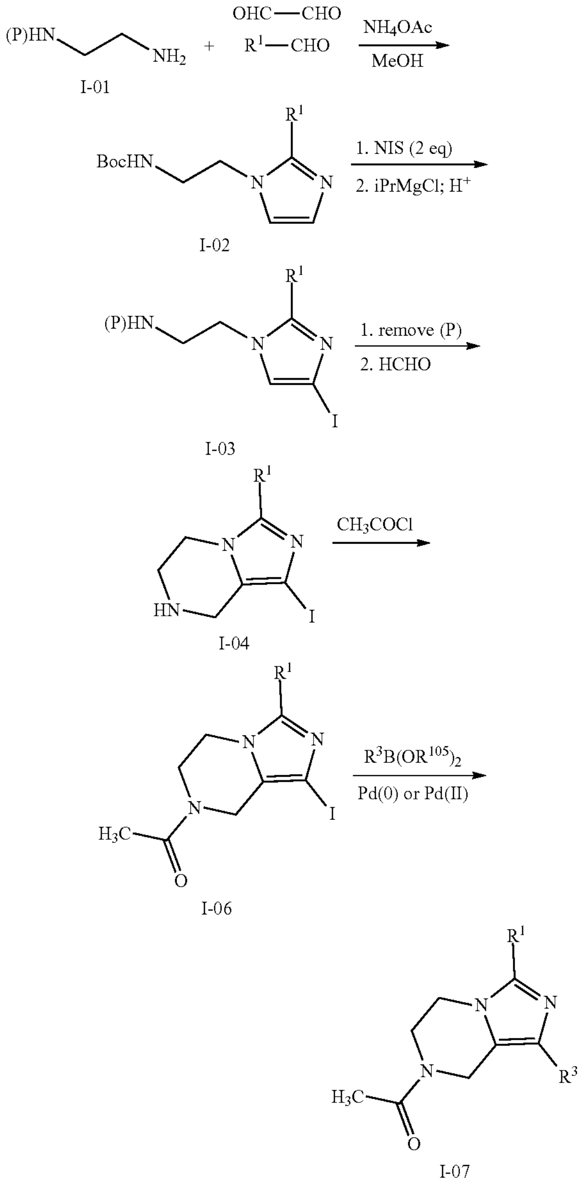

I-01

I-02

I-03

I-04

I-06

I-07

The Examples can be synthesized using the following general synthetic procedure set forth in Scheme I. Synthesis of imidazole I-02 begins with ethylenediamine I-01 having a suitable protecting group symbolized as (P), such as a carbamate protecting group. Compound I-01 is reacted with glyoxal and aldehyde $R^1$—CHO. Mono-iodo compound I-03 is formed through a 2-step procedure that consists of the synthesis of the 4,5-diiodoimidazole compound (not shown), followed by selective halogen/metal exchange and $H^+$ quench of the resulting organometallic. The protecting group is removed (for example, a Boc group is removed with HCl), and condensation with formaldehyde gives the bicyclic structure. The amino group can be functionalized with acetyl chloride (or an equivalent, such as acetic anhydride) to give amide I-06. Synthesis is completed by Pd(II)-mediated coupling of I-06 with an arylboronic acid or ester to give I-07.

Scheme II

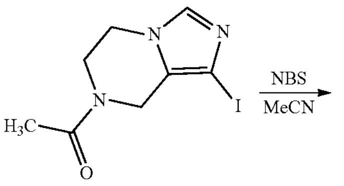

I-06

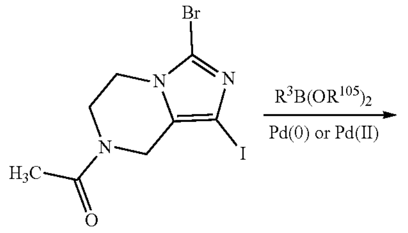

II-01

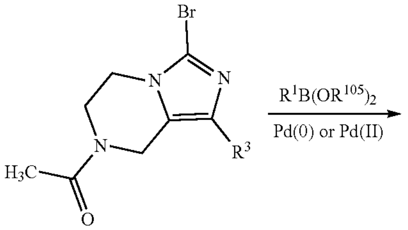

II-02

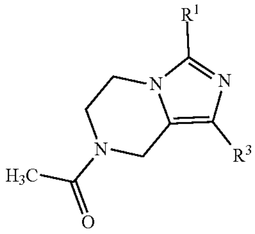

II-03

Other Examples can be synthesized using the following general synthetic procedure set forth in Scheme II. Reaction of I-06 with NBS provides the bromo-iodo intermediate II-01, which can be selectively reacted twice under Suzuki coupling conditions to provide first II-02 then II-03.

Scheme III

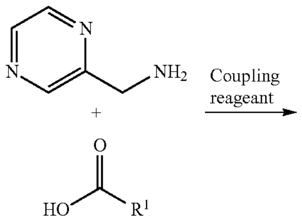

III-01

-continued

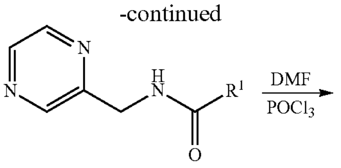

III-02

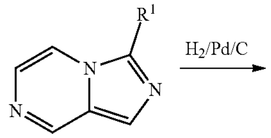

III-03

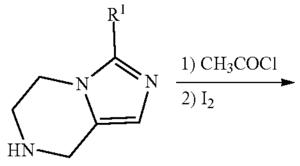

III-04

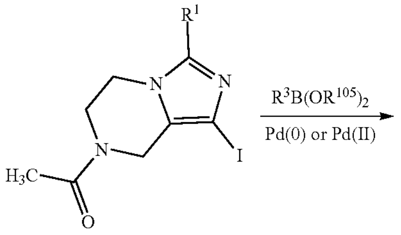

III-05

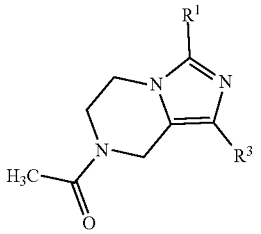

III-06

Other Examples can be synthesized using the general synthetic procedure set forth in Scheme III. Coupling of acid III-01 with pyrazin-2-ylmethanamine provides amide III-02, which is cyclized to provide imidazopyrazine III-03. Imidazopyrazine III-03 is reduced by hydrogenation to imidazopiperazine III-04. Imidazopiperazine III-04 is reacted with acetyl chloride (or an equivalent, such as acetic anhydride) followed by reaction with iodine to provide amide III-05. Synthesis is completed by Pd(II)-mediated coupling of III-05 with an arylboronic ester or acid to give III-06, respectively.

The disclosure is further illustrated by the following examples.

Intermediate "A"

1-(3-Cyclopropyl-1-iodo-5,6-dihydroimidazo[1,5-α] pyrazin-7 (8H)-yl)ethan-1-one

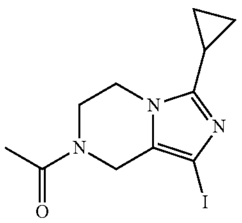 [SMILES: CC(=O)N1CCn2c(C3CC3)nc(I)c2C1]

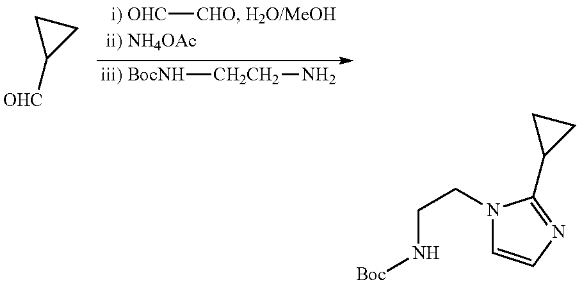

tert-Butyl (2-(2-cyclopropyl-1H-imidazol-1-yl)ethyl)carbamate

To a solution of cyclopropanecarbaldehyde (0.70 g, 10 mmol) in MeOH (50 ml) at RT was added tert-butyl (2-aminoethyl)carbamate (1.60 g, 10 mmol) followed by $NH_4OAc$ (0.771 g, 10.0 mmol) and 40% aqueous glyoxal (1.451 g, 10.00 mmol). The mixture was stirred at RT for 16 h, then concentrated under reduced pressure. Sat. aq. $NaHCO_3$ (50 mL) was added, the aqueous phase was extracted with EtOAc (3×20 mL), and the combined organic layers were washed with sat. aq. NaCl, dried over $MgSO_4$, filtered and concentrated under reduced pressure to give the crude title compound as a yellow foamy solid (2.51 g), which was used in the next step without further purification. MS ($ES^+$) $C_{13}H_{21}N_3O_2$ requires: 251 found: 252 $[M+H]^+$.

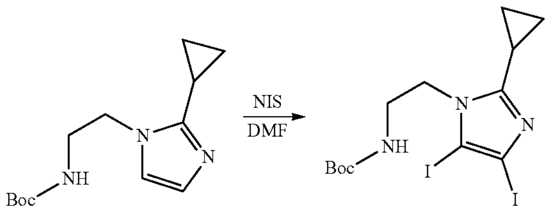

tert-Butyl (2-(2-cyclopropyl-4,5-diiodo-1H-imidazol-1-yl)ethyl)carbamate

To a solution of the crude product from the previous step (2.51 g, 10.0 mmol) in DMF (30 ml) was added NIS (6.75 g, 30.0 mmol), and the resulting mixture was stirred at 80° C. for 2 h, then allowed to cool to RT. $H_2O$ (100 mL) and sat. aq. $Na_2S_2O_3$ (5 ml) were added. The aqueous phase was extracted with EtOAc (3×50 mL), and the combined organic layers were washed with sat. aq. NaCl, dried over $MgSO_4$, filtered and concentrated under reduced pressure. The residue was purified by $SiO_2$ gel chromatography (0% to 50% EtOAc in hexanes) to give the title compound as a pale yellow foamy solid (2.41 g, 48%). MS ($ES^+$) $C_{13}H_{19}I_2N_3O_2$ requires: 503, found: 504 $[M+H]^+$.

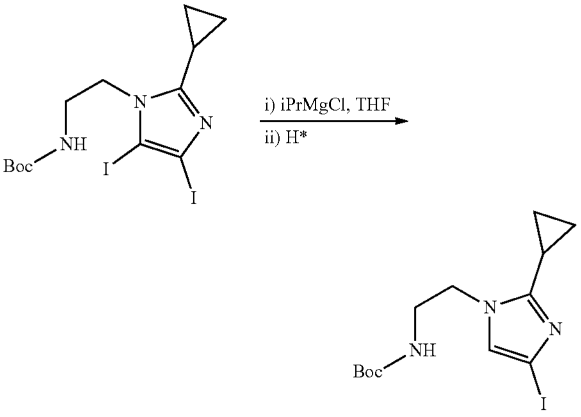

tert-Butyl (2-(2-cyclopropyl-4-iodo-1H-imidazol-1-yl)ethyl)carbamate

To a solution of the product from the previous step (2.40 g, 4.77 mmol) in THF (20 ml) at −78° C. was added 2.0 M iPrMgCl in THF (3.58 ml, 7.16 mmol), and the resulting mixture was stirred at −78° C. for 0.5 h. Sat. aq. $NH_4Cl$ (50 mL) was added, and the layers were separated. The aqueous phase was extracted with EtOAc (3×30 mL), and the combined organic layers were washed with sat. aq. NaCl, dried over $MgSO_4$, filtered and concentrated under reduced pressure. The residue was purified by $SiO_2$ gel chromatography (0% to 60% EtOAc in hexanes) to give the title compound as an off-white solid (1.45 g, 81%). MS ($ES^+$) $C_{13}H_{20}IN_3O_2$ requires: 377, found: 378 $[M+H]^+$.

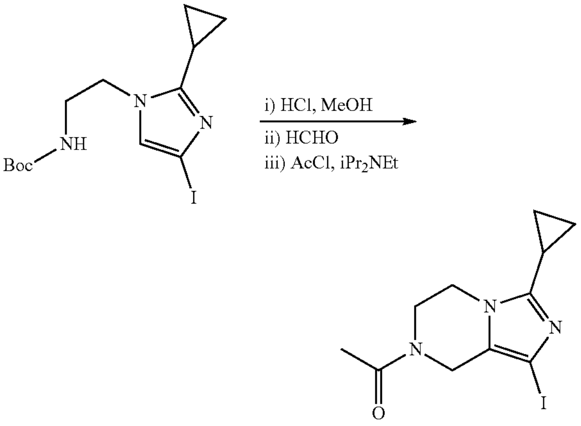

1-(3-Cyclopropyl-1-iodo-5,6-dihydroimidazo[1,5-α] pyrazin-7 (8H)-yl)ethan-1-one

To a solution of HCl in MeOH (made by adding AcCl (2 mL) dropwise to MeOH (10 mL)) was added the product from the previous step (700 mg, 1.86 mmol), and the resulting mixture was stirred at RT for 1 h. The mixture was concentrated under reduced pressure, and the residue was dissolved in EtOH (10 ml). To the resulting mixture was added 50% aq. HCHO (2.045 ml, 37.1 mmol), and the mixture was stirred at 100° C. for 3 h then concentrated under reduced pressure. The residue was dissolved in $CH_2Cl_2$ (10 ml), and the resulting mixture was cooled to 0° C. then treated with $iPr_2NEt$ (0.972 ml, 5.57 mmol) and acetyl chloride (0.198 ml, 2.78 mmol). The mixture was stirred at RT for 1 h, then concentrated under reduced pressure. The residue was treated with $H_2O$ (20 mL), extracted with EtOAc (3×10 mL), and the combined organic layers were washed with sat. aq. NaCl, dried over $MgSO_4$, filtered and concentrated under reduced pressure. The residue was purified by $SiO_2$ gel chromatography (0% to 5% MeOH in $CH_2Cl_2$) to give the title compound as an off-white solid (355 mg, 58%). MS ($ES^+$) $C_{11}H_{14}IN_3O$ requires: 331, found: 332 $[M+H]^+$.

Intermediate "B"

1-(1-Iodo-3-(tetrahydro-2H-pyran-4-yl)-5,6-dihydroimidazo[1,5-α]pyrazin-7 (8H)-yl)ethanone

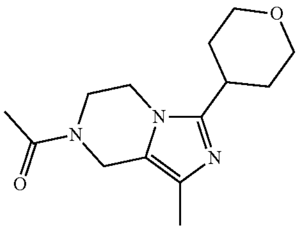 [SMILES: CC(=O)N1CCn2c(C3CCOCC3)nc(C)c2C1]

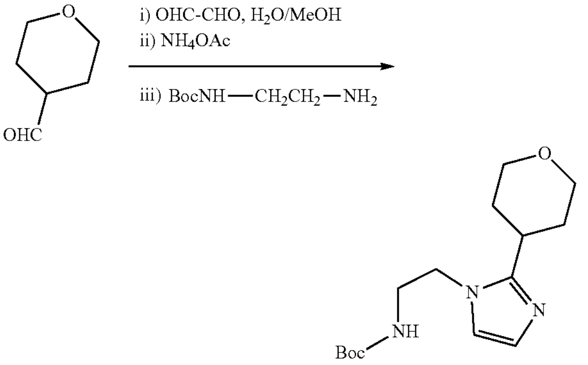

tert-Butyl 2-(2-(tetrahydro-2H-pyran-4-yl)-1H-imidazol-1-yl)ethylcarbamate.

To a mixture of tetrahydro-2H-pyran-4-carbaldehyde (2.80 g, 25 mmol) and 40% aq. glyoxal (5.0 g, 34 mmol) in MeOH (100 mL) at 0° C. was added $NH_4OAc$ (3.8 g, 49 mmol), followed by tert-butyl 2-aminoethylcarbamate (3.94 g, 24.6 mmol) dropwise. The mixture was stirred at RT overnight, then concentrated under reduced pressure. The residue was diluted with MeOH/$CH_2Cl_2$ (1/10, 400 mL), and the mixture was washed with sat. aq. $NH_4Cl$ (200 mL), dried over $Na_2SO_4$, filtered and concentrated under reduced pressure to afford the crude title compound as a red oil (7.0 g, 96%). MS ($ES^+$) $C_{15}H_{25}N_3O_3$ requires: 295, found: 296 $[M+H]^+$.

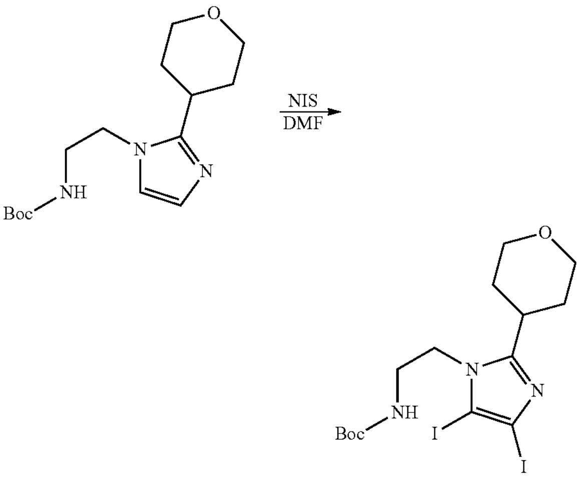

tert-Butyl 2-(4,5-diiodo-2-(tetrahydro-2H-pyran-4-yl)-1H-imidazol-1-yl)ethylcarbamate.

To a mixture of the product from the previous step (7.0 g, 24 mmol) in DMF (80 mL) at 0° C. was added NIS (16 g, 71 mmol) in small portions. The mixture was stirred at RT overnight, diluted with $H_2O$ (800 mL), and extracted with EtOAc (300 mL×3). The combined organic layers were washed with sat. aq. $NH_4Cl$ (200 mL×4), dried over $Na_2SO_4$, filtered and concentrated under reduced pressure. The residue was purified by $SiO_2$ gel chromatography (0% to 40% EtOAc in petroleum ether) to give the title compound as a tan solid (4.3 g, 33%). MS ($ES^+$) $C_{15}H_{23}I_2N_3O_3$ requires: 547, found: 548 $[M+H]^+$.

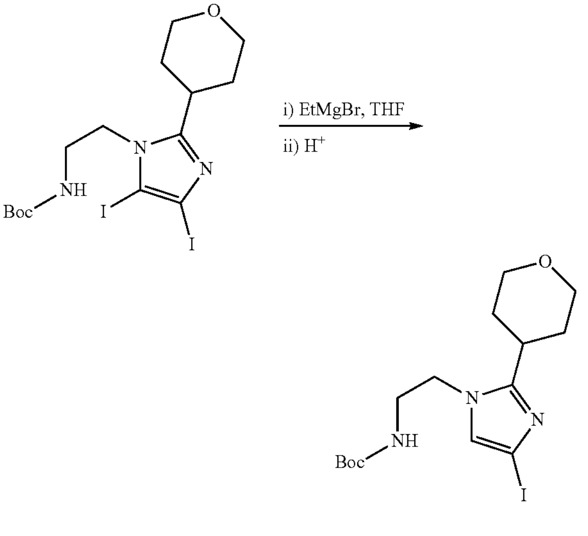

tert-Butyl 2-(4-iodo-2-(tetrahydro-2H-pyran-4-yl)-1H-imidazol-1-yl)ethylcarbamate.

To a mixture of the product from the previous step (4.3 g, 7.9 mmol) in THF (100 mL) at −50° C. was added, dropwise, 1.0 M EtMgBr in THF (31.6 mL, 31.6 mmol). The mixture was stirred at −50° C. for 3 h, treated with sat. aq. $NH_4Cl$ (10 mL) at low temperature, diluted with $H_2O$ (200 mL), and extracted with EtOAc (100 mL×3). The combined organic phases were washed with sat. aq. NaCl (100 mL), dried over $Na_2SO_4$, filtered and concentrated under reduced pressure to give the crude title compound as a yellow oil (3.1 g, 93%). MS ($ES^+$) $C_{15}H_{24}IN_3O_3$ requires: 421, found: 422 $[M+H]^+$.

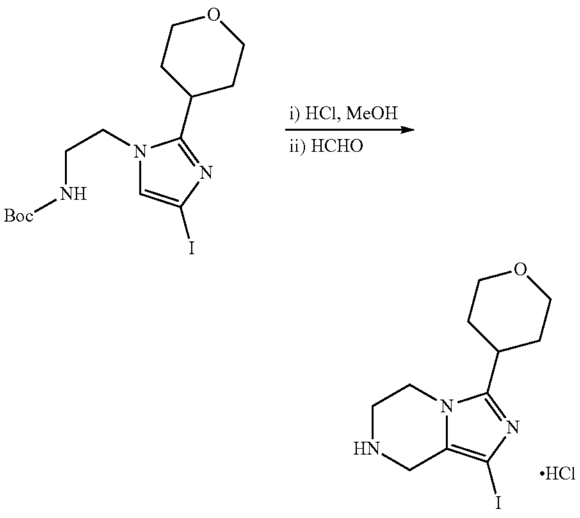

1-Iodo-3-(tetrahydro-2H-pyran-4-yl)-5,6,7,8-tetrahydroimidazo[1,5-α]pyrazine, HCl salt.

The product from the previous step (3.1 g, 7.4 mmol) was treated with 2 M HCl in MeOH (50 mL, 100 mmol). The mixture was stirred at RT for 3 h, then concentrated under reduced pressure. The residue was dissolved in EtOH (50 mL), and the mixture was treated with paraformaldehyde (6.66 g, 222 mmol). The mixture was stirred at reflux for 2 h, then allowed to cool to RT. The solid was collected by filtration and washed with EtOH (10 mL) to give the title compound as a white solid (1.8 g, 66%). MS ($ES^+$) $C_{11}H_{16}IN_3O$ requires: 333, found: 334 $[M+H]^+$.

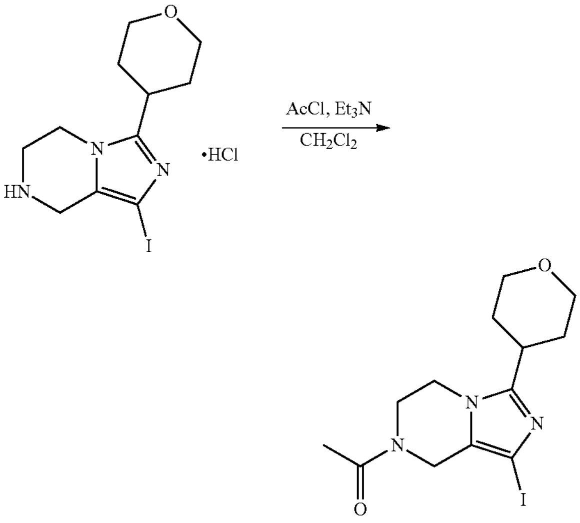

1-(1-Iodo-3-(tetrahydro-2H-pyran-4-yl)-5,6-dihydroimidazo[1,5-α]pyrazin-7 (8H)-yl)ethan-1-one.

To a suspension of the product from the previous step (25.0 g, 67.6 mmol) in $CH_2Cl_2$ (200 ml) at 0° C. were added $Et_3N$ (28.3 ml, 203 mmol) and AcCl (5.77 ml, 81.0 mmol) and the resulting mixture was stirred at 0° C. for 0.5 h. Sat.

aq. NaCl (100 mL) was added, and white solid was removed by filtration. The filtrate layers were separated, the aqueous phase was extracted with $CH_2Cl_2$ (3×200 mL), and the combined organic layers were dried over $MgSO_4$, filtered and concentrated under reduced pressure. The residue was purified by $SiO_2$ gel chromatography (0% to 8% MeOH in $CH_2Cl_2$) to give the title compounds as a white solid (25.4 g, 100%). MS ($ES^+$) $C_{13}H_{18}IN_3O_2$ requires: 375, found: 376 $[M+H]^+$.

Intermediate "C"

N-methyl-5-(8-(4,4,5,5-tetramethyl-1,3,2-dioxaborolan-2-yl)isoquinolin-3-yl)picolinamide

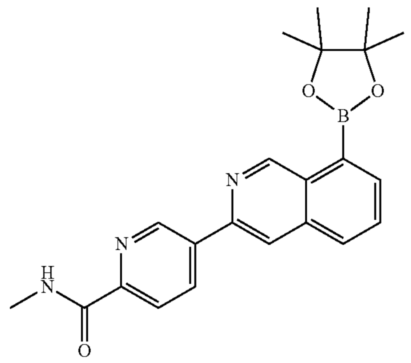

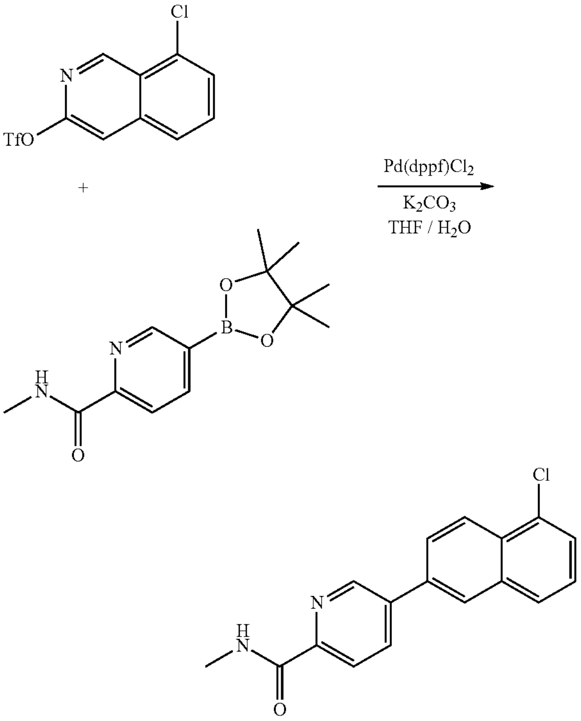

5-(8-Chloroisoquinolin-3-yl)-N-methylpicolinamide

A mixture of 8-chloroisoquinolin-3-yl trifluoromethanesulfonate (11.9 g, 38.2 mmol), N-methyl-5-(4,4,5,5-tetramethyl-1,3,2-dioxaborolan-2-yl)picolinamide (10.0 g, 38.2 mmol), Pd (dppf) $Cl_2$ (2.80 g, 3.82 mmol) and $K_2CO_3$ (13.8 g, 100 mmol) in THF (250 mL) and $H_2O$ (50 ml) was stirred at 80° C. for 3 h. The mixture was poured into water (400 mL) and extracted with EtOAc (400 mL×3). The combined organic layers were dried over $Na_2SO_4$, filtered and concentrated under reduced pressure. The residue was purified by $SiO_2$ gel chromatography (70% to 90% petroleum ether in EtOAc) to give the title compound as a yellow solid (330 mg, 73%). MS ($ES^+$) $C_{16}H_{12}ClN_3O$ requires: 297, found: 298 $[M+H]^+$.

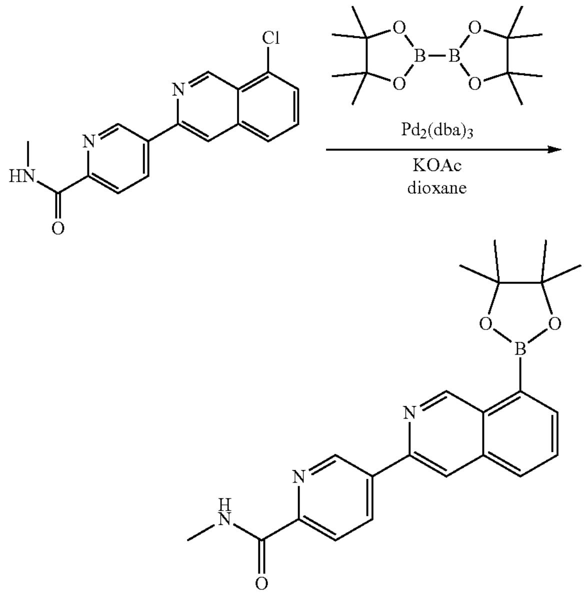

N-Methyl-5-(8-(4,4,5,5-tetramethyl-1,3,2-dioxaborolan-2-yl)isoquinolin-3-yl)picolinamide.

A suspension of the product from the previous step (3.5 g, 11.8 mmol), $Pd_2(dba)_3$ (1.08 g, 1.18 mmol), $Cy_3P$ (1.32 g, 4.72 mmol), AcOK (3.43 g, 35.0 mmol) and $B_2Pin_2$ (4.58 g, 18.0 mmol) in dioxane (200 mL) was stirred at 120° C. overnight. The mixture was poured into water (400 mL) and extracted with EtOAc (400 mL×3). The combined organic layers were dried over $Na_2SO_4$, filtered and concentrated under reduced pressure. The residue was purified by $SiO_2$ gel chromatography (70% to 100% EtOAc in petroleum ether) to give the title compound as a yellow solid (4.1 g, 89%). MS ($ES^+$) $C_{22}H_{24}BN_3O_3$ requires: 389, found 390 $[M+H]^+$.

Intermediate "D"

8-Chloro-7-fluoroisoquinolin-3-yl trifluoromethanesulfonate

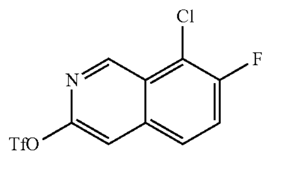 [SMILES: O=S(=O)(Oc1cc2ccc(F)c(Cl)c2cn1)C(F)(F)F]

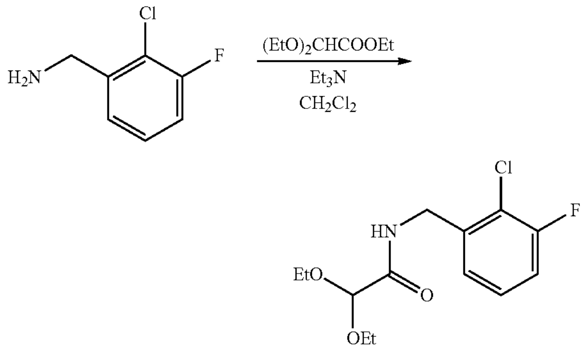

N-(2-Chloro-3-fluorobenzyl)-2,2-diethoxyacetamide.

To a mixture of (2-chloro-3-fluorophenyl) methanamine (12 g, 75 mmol) and ethyl 2,2-diethoxyacetate (19.93 g, 113.2 mmol) in MeOH (120 mL) was added $Et_3N$ (22.87 g, 226.4 mmol), and the mixture was stirred at 80° C. overnight then concentrated under reduced pressure. The residual oil was poured into water (150 mL) and the mixture was extracted with $Et_2O$ (150 ml×3). The combined organic layers were dried over $Na_2SO_4$, filtered and concentrated under reduced pressure. The residue was purified by $SiO_2$ gel chromatography (40% to 60% EtOAc in petroleum ether) to give the title compound as a yellow solid (17.3 g, 79%). MS ($ES^+$) $C_{13}H_{17}ClFNO_3$ requires: 289, found: 290 $[M+H]^+$.

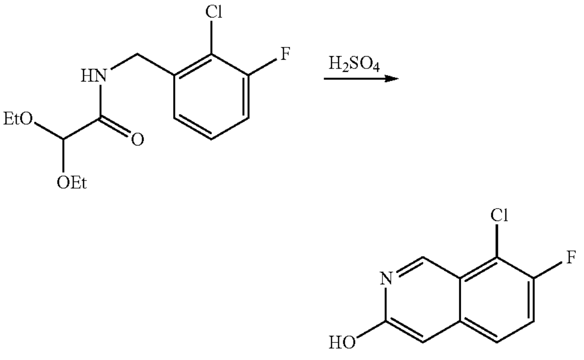

8-Chloro-7-fluoroisoquinolin-3-ol

The product from the previous step (17.3 g, 59.9 mmol) was dissolved in conc. aq. $H_2SO_4$ (200 ml), and the mixture was stirred at RT overnight. The mixture was poured into ice water (400 mL), the pH was adjusted to 7, and the mixture was extracted with $Et_2O$ (400 ml×3). The combined organic layers were dried over $Na_2SO_4$, filtered and concentrated under reduced pressure to give the crude title compound as a yellow solid (15.8 g).

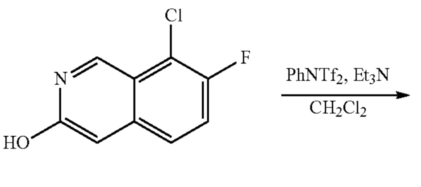

-continued

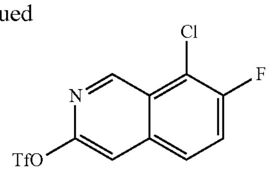

8-Chloro-7-fluoroisoquinolin-3-yl trifluoromethanesulfonate

A mixture of the product from the previous step (15.8 g, 80.2 mmol), 1,1,1-trifluoro-N-phenyl-N-(trifluoromethylsulfonyl) methanesulfonamide (34.36 g, 96.24 mmol), and $Et_3N$ (24.3 g, 241 mmol) in $CH_2Cl_2$ (500 ml) was stirred at RT for 3 h, then poured into water (500 mL) and extracted with $CH_2Cl_2$ (500 mL×3). The combined organic layers were dried over $Na_2SO_4$, filtered and concentrated under reduced pressure. The residue was purified by $SiO_2$ gel chromatography (3% to 5% EtOAc in petroleum ether) to give the title compound as a yellow solid (14.7 g, 75%). MS ($ES^+$) $C_{10}H_4ClF_4NO_3S$ requires: 329, found: 330 $[M+H]^+$.

Example 1

1-(1-(3-(2-methylthiazol-5-yl)isoquinolin-8-yl)-3-(tetrahydro-2H-pyran-4-yl)-5,6-dihydroimidazo[1,5-α]pyrazin-7 (8H)-yl)ethan-1-one

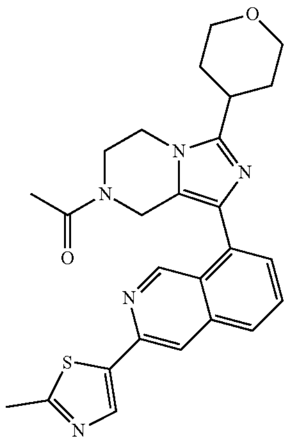 [SMILES: CC(=O)N1CCn2c(C3CCOCC3)nc(-c3cccc4cc(-c5cnc(C)s5)ncc34)c2C1]

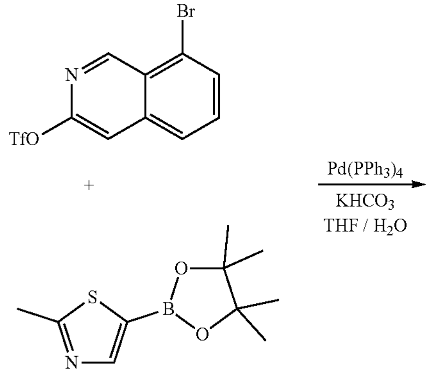

-continued

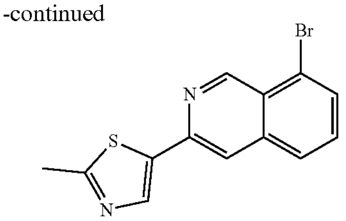

5-(8-Bromoisoquinolin-3-yl)-2-methylthiazole

A mixture of 8-bromoisoquinolin-3-yl trifluoromethanesulfonate (0.90 g, 2.5 mmol), 2-methyl-5-(4,4,5,5-tetramethyl-1,3,2-dioxaborolan-2-yl) thiazole (0.57 g, 2.5 mmol), $NaHCO_3$ (0.63 g, 7.5 mmol) and $Pd(PPh_3)$ 4 (280 mg, 0.25 mmol) in $THF/H_2O$ (20 mL/4 mL) was degassed and purged with $N_2$, then stirred at 50° C. overnight. The mixture was concentrated under reduced pressure, and the residue was purified by $SiO_2$ gel chromatography (0% to 50% EtOAc in petroleum ether) to give the title compound as a yellow solid (450 mg, 60%). MS ($ES^+$): $C_{13}H_9BrN_2S$ requires: 304, found: 305 $[M+H]^+$.

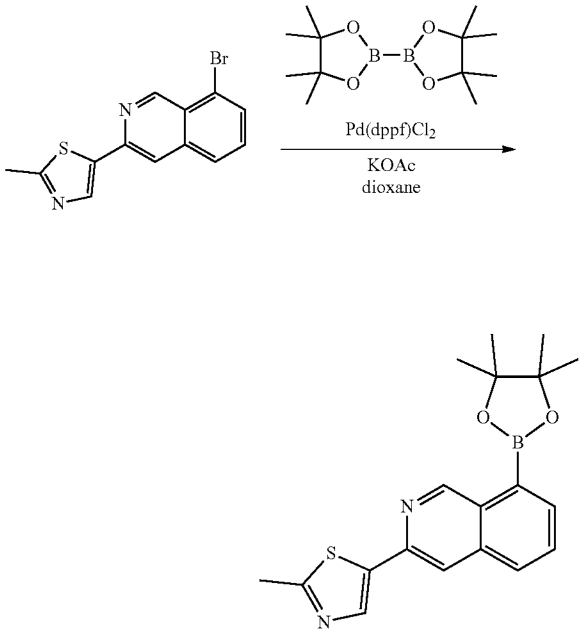

2-Methyl-5-(8-(4,4,5,5-tetramethyl-1,3,2-dioxaborolan-2-yl)isoquinolin-3-yl) thiazole To a mixture of the product of the previous step (450 mg, 1.48 mmol), $B_2Pin_2$ (450 mg, 1.78 mmol) and KOAc (435 mg, 4.44 mmol) in dioxane (20 mL) was added $PdCl_2$ (dppf) (120 mg, 0.15 mmol). The resulting mixture was purged with $N_2$ for 5 min, then sealed and stirred at 100° C. overnight. The mixture was concentrated under reduced pressure, and the residue was purified by $SiO_2$ gel chromatography (0% to 100% EtOAc in petroleum ether) to give the title compound as a yellow solid (400 mg, 76%). MS ($ES^+$): $C_{19}H_{21}BN_2O_2S$ requires: 352, found: 353 $[M+H]^+$.

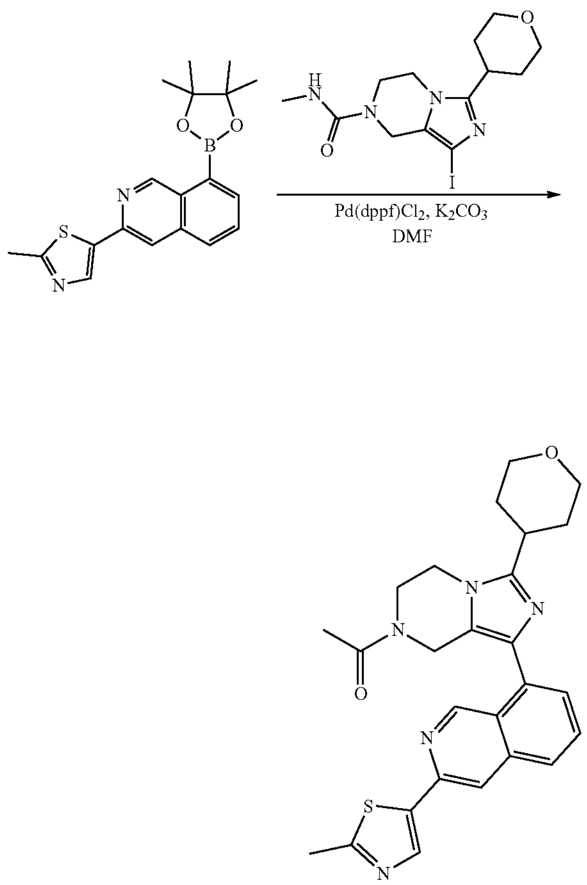

1-(1-(3-(2-Methylthiazol-5-yl)isoquinolin-8-yl)-3-(tetrahydro-2H-pyran-4-yl)-5,6-dihydroimidazo[1,5-α]pyrazin-7(8H)-yl)ethanone To a suspension of Intermediate "B" (30 g, 80 mmol) in DMF (400 ml) was added the product from the previous step (28.2 g, 80.0 mmol), $PdCl_2$ (dppf)-$CH_2Cl_2$ (3.26 g, 4.00 mmol) and 2.0 M aq. $K_2CO_3$ (80 ml, 160 mmol). The mixture was degassed by bubbling with $N_2$ for 5 min, and the resulting mixture was then stirred under $N_2$ at 100° C. for 2 h. The reaction was allowed to cool to RT, then treated with sat. aq. NaCl (200 mL), and the solid was removed by filtration. The mixture was extracted with EtOAc (3×300 mL), and the combined organic layers were dried over $MgSO_4$, filtered and concentrated under reduced pressure. The resulting residue was triturated with EtOAc and precipitate was isolated to give the desired product. The filtrate was concentrated under reduced pressure, and the residue was purified by $SiO_2$ gel chromatography (0% to 15% MeOH in $CH_2Cl_2$) to give desired product, which was combined with the above precipitated product, to give the title compound as an off-white solid (13.5 g, 36%).

MS ($ES^+$) $C_{26}H_{27}N_5O_2S$ requires: 473, found: 474 $[M+H]^+$.

$^1$H NMR (400 MHZ, DMSO-$d_6$) (ca. 2:1 mixture of rotamers) δ 9.97 (s, 1H), 8.38-8.37 (m, 2H), 7.96-7.74 (m, 2H), 7.56-7.47 (m, 1H), 4.87 (s, 0.7H), 4.79 (d, 1.3H), 4.30-4.04 (m, 2H), 4.00-3.92 (m, 4H), 3.59-3.38 (m, 2H), 3.12 (quint, J=7.4 Hz, 1H), 2.71 (s, 3H), 2.11 (s, 2H), 2.04 (s, 1H), 1.94-1.71 (m, 4H).

Example 2

5-(8-(7-Acetyl-3-cyclopropyl-5,6,7,8-tetrahydroimidazo[1,5-α]pyrazin-1-yl)isoquinolin-3-yl)-N-methylpicolinamide

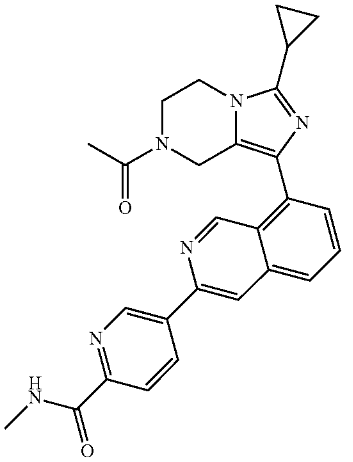 [SMILES: CNC(=O)c1ccc(-c2cc3cccc(-c4nc(C5CC5)n5c4CN(C(C)=O)CC5)c3cn2)cn1]

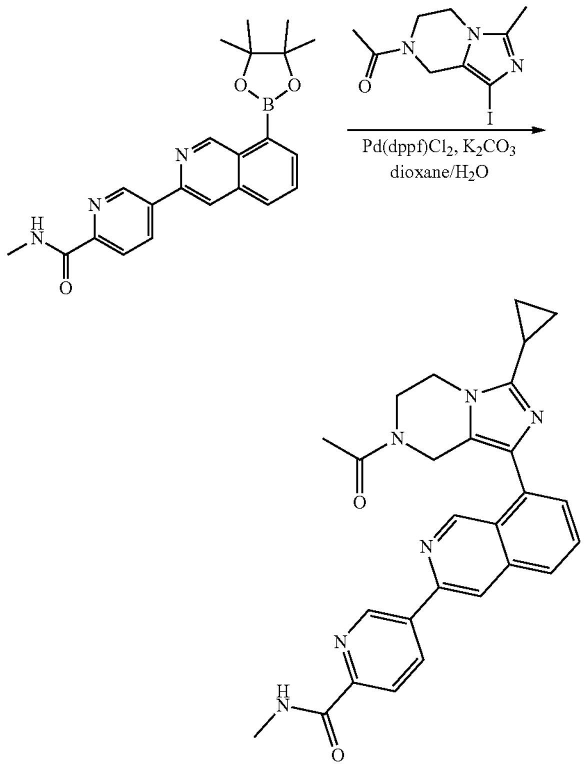

To a degassed solution of Intermediate "A" (83 mg, 0.25 mmol) in 4:1 dioxane/water (3 mL) was added Intermediate "C" (100 mg, 0.25 mmol), $K_2CO_3$ (69 mg, 0.50 mmol), and Pd (dppf) $Cl_2$ (20 mg, 0.025 mmol), and the resulting mixture was stirred at 100° C. for 2 h. The mixture was concentrated under reduced pressure, and the residue was purified by reverse phase preparative HPLC (Mobile phase:

A=0.1% $NH_4HCO_3/H_2O$, B=MeCN; Gradient: B=35% to 75% in 14 min; Column: C18) to give the title compound as a white solid (28 mg, 24%).

MS ($ES^+$): $C_{27}H_{26}N_6O_2$ requires: 466, found: 467 $[M+H]^+$.

$^1H$ NMR (500 MHZ, $CDCl_3$) (ca. 2:1 mixture of rotamers) δ 9.83-9.82 (m, 1H), 9.41-9.22 (m, 1H), 8.68-8.43 (m, 1H), 8.35-8.32 (m, 1H), 8.17-8.11 (m, 2H), 7.93-7.57 (m, 2H), 7.57-7.43 (m, 1H), 4.87 (s, 0.7H), 4.75 (s, 1.3H), 4.37-3.83 (m, 4H), 3.08 (d, J=5.0 Hz, 3H), 2.24 (s, 1H), 2.12 (s, 2H), 1.95-1.81 (m, 1H), 1.18-1.04 (m, 4H).

Example 3

5-(8-(7-Acetyl-3-(tetrahydro-2H-pyran-4-yl)-5,6,7,8-tetrahydroimidazo[1,5-α]pyrazin-1-yl)isoquinolin-3-yl)-N-methylpicolinamide

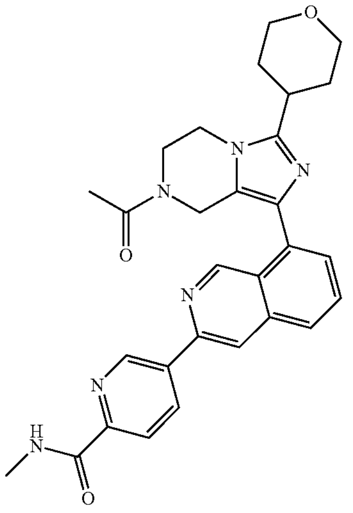 [SMILES: CNC(=O)c1ccc(-c2cc3cccc(-c4nc(C5CCOCC5)n5c4CN(C(C)=O)CC5)c3cn2)cn1]

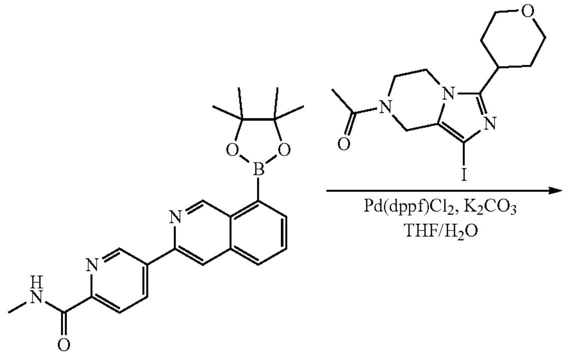

-continued

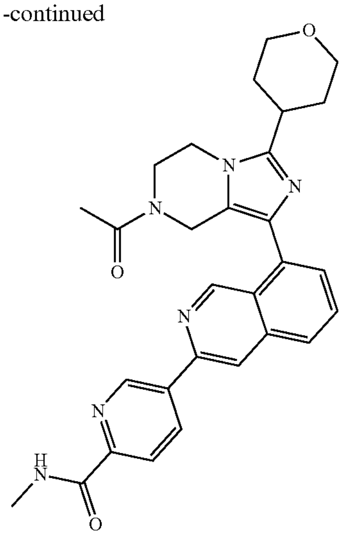

A suspension of Intermediate "C" (7.00 g, 18.0 mmol), Intermediate "B" (6.75 g, 18.0 mmol), Pd (dppf) $Cl_2$ (1.32 g, 1.80 mmol), and $K_2CO_3$ (7.5 g, 54 mmol) in THF (200 mL) and water (40 ml) was degassed by purging with $N_2$, and the mixture was stirred under $N_2$ at 80° C. for 3 h. The mixture was poured into water (400 mL) and extracted with EtOAc (400 mL×3). The combined organic layers were dried over $Na_2SO_4$, filtered and concentrated under reduced pressure. The residue was purified by $SiO_2$ gel chromatography (0% to 10% MeOH in EtOAc) to give the title compound as a yellow solid (4.6 g, 50%).

MS ($ES^+$) $C_{29}H_{30}N_6O_3$ required: 510, found: 511 $[M+H]^+$.

$^1H$ NMR (500 MHZ, $CD_3OD$) (ca. 2:1 mixture of rotamers) δ 9.70 (s, 0.3H), 9.69 (s, 0.7H), 9.40 (br s, 1H), 8.68-8.67 (m, 1H), 8.49 (s, 0.3H), 8.48 (s, 0.7H), 8.23 (appar d, J=8.2 Hz, 1H), 8.09-8.06 (m, 1H), 7.91-7.87 (m, 1H), 7.71-7.66 (m, 1H), 4.86 (s, 0.7H), 4.82 (s, 1.3H), 4.33 (t, J=5.5 Hz, 1.3H), 4.23 (t, J=5.4 Hz, 0.7H), 4.15-4.01 (m, 4H), 3.65 (t, J=11.8 Hz, 2H), 3.26-3.21 (m, 1H), 3.03 (s, 3H), 2.24 (s, 2H), 2.12 (s, 1H), 2.12-2.02 (m, 2H), 1.98-1.83 (m, 2H).

Example 4

5-(8-(7-acetyl-3-(2-oxabicyclo[2.2.2]octan-4-yl)-5,6,7,8-tetrahydroimidazo[1,5-α]pyrazin-1-yl)isoquinolin-3-yl)-N-methylpicolinamide

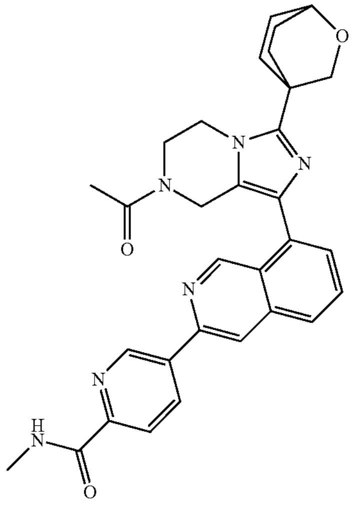 [SMILES: CNC(=O)c1ccc(-c2cc3cccc(-c4nc(C56CCC(CC5)OC6)n5c4CN(C(C)=O)CC5)c3cn2)cn1]

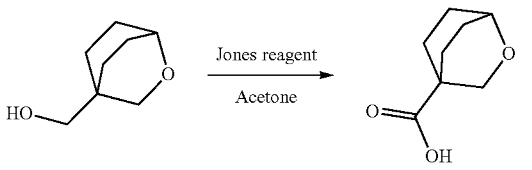 [SMILES: OCC12CCC(CC1)OC2 ; O=C(O)C12CCC(CC1)OC2]

2-Oxabicyclo[2.2.2]octane-4-carboxylic acid

To a mixture of 2-oxabicyclo[2.2.2]octan-4-ylmethanol (3.00 g, 21.1 mmol) in acetone (50 mL) at 0° C. was added Jones reagent (18.6 mL, 49.7 mmol). The mixture was stirred at RT for 1 h, then diluted with water (50 mL) and extracted with EtOAc (50 mL×3). The combined organic layers were washed with sat. aq. NaCl (25 mL), dried over $Na_2SO_4$, filtered and concentrated under reduced pressure. The residue was purified by $SiO_2$ gel chromatography (0% to 10% MeOH in $CH_2Cl_2$) to give the title compound as a white solid (2.73 g, 83%). MS ($ES^-$):$C_8H_{12}O_3$ requires: 156, found: 155 $[M-H]^-$.

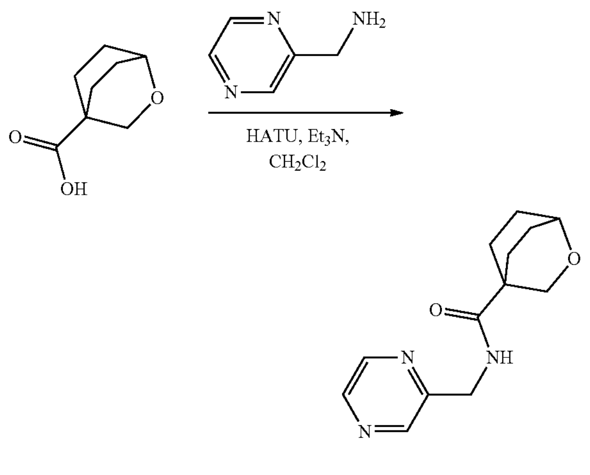

N-(Pyrazin-2-ylmethyl)-2-oxabicyclo[2.2.2]octane-4-carboxamide

To a mixture of the product from the previous step (2.73 g, 17.5 mmol), pyrazin-2-ylmethanamine (2.10 g, 19.2 mmol) and DIEA (8.67 mL, 2.44 mmol) in DMF (45 mL) was added HATU (7.31 g, 19.2 mmol). The mixture was stirred at RT for 1 h, then concentrated under reduced pressure. The residue was purified by $SiO_2$ gel chromatography (0% to 5% MeOH in $CH_2Cl_2$) to give the title compound as a yellow solid (3.30 g, 76%). MS ($ES^+$): $C_{13}H_{17}N_3O_2$ requires: 247, found: 248 $[M+H]^+$.

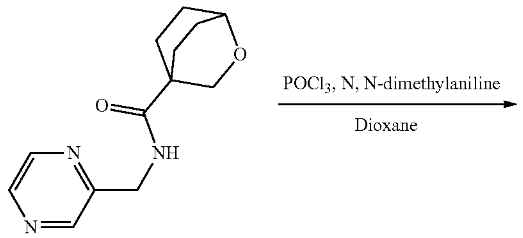

-continued

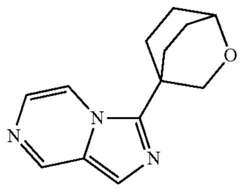

3-(2-Oxabicyclo[2.2.2]octan-4-yl) imidazo[1,5-α]pyrazine

To a solution of the product from the previous step (2.00 g, 8.09 mmol) and N,N-dimethylaniline (206.33 μL, 1.62 mmol) in dioxane (160 mL) were added phosphorus oxychloride (3.77 mL, 40.4 mmol) and $Et_3N$ (3.37 mL, 24.3 mmol). The resulting mixture was stirred at 90° C. for 4 h, then partially concentrated under reduced pressure. The residue was treated with sat. aq. $NaHCO_3$ (50 mL) with ice, and layers were separated. The aqueous phase was extracted with EtOAc (3×100 mL), and the combined organic layers were washed with sat. aq. NaCl, dried over $MgSO_4$, filtered and concentrated under reduced pressure. The residue was purified by $SiO_2$ gel chromatography (0% to 10% MeOH in $CH_2Cl_2$) to give the title compound as a yellow solid (819.00 mg, 44%). MS ($ES^+$): $C_{13}H_{15}N_3O$ requires: 229, found: 230 $[M+H]^+$.

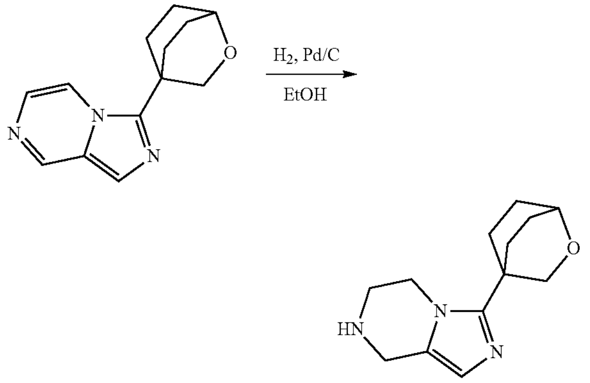

3-(2-Oxabicyclo[2.2.2]octan-4-yl)-5,6,7,8-tetrahydroimidazo[1,5-α]pyrazine

To a mixture of the product from the previous step (1.51 g, 6.59 mmol) in EtOH (90 mL) was added 10% Pd/C (1.00 g, 940 μmol). The mixture was stirred under $H_2$ (balloon) at RT for 5 h, then filtered and concentrated under reduced pressure to obtain the title compound as a yellow solid (1.55 g, quant.). MS ($ES^+$): $C_{13}H_{19}N_3O$ requires: 233, found: 234 $[M+H]^+$.

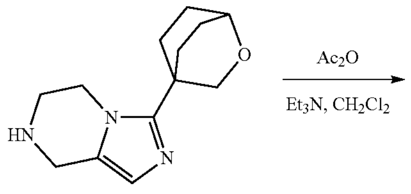

-continued

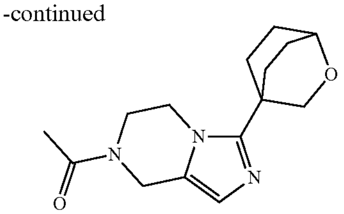

1-(3-(2-Oxabicyclo[2.2.2]octan-4-yl)-5,6-dihydroimidazo [1,5-α]pyrazin-7 (8H)-yl)ethanone To a solution of the product from the previous step (1.55 g, 6.64 mmol) in $CH_2Cl_2$ (75 mL) at 0° C. were added $Et_3N$ (2.77 mL, 19.9 mmol) and acetic anhydride (935.92 μL, 9.90 mmol). The resulting mixture was stirred for 1 h then treated with sat. aq. $NaHCO_3$ and extracted with $CH_2Cl_2$ (75 mL×3). The combined organic layers were washed with sat. aq. NaCl (45 mL), dried over $Na_2SO_4$, filtered and concentrated under reduced pressure to give the title compound as a yellow oil (1.40 g, 77%). MS ($ES^+$): $C_{15}H_{21}N_3O_2$ requires: 275, found: 276 $[M+H]^+$.

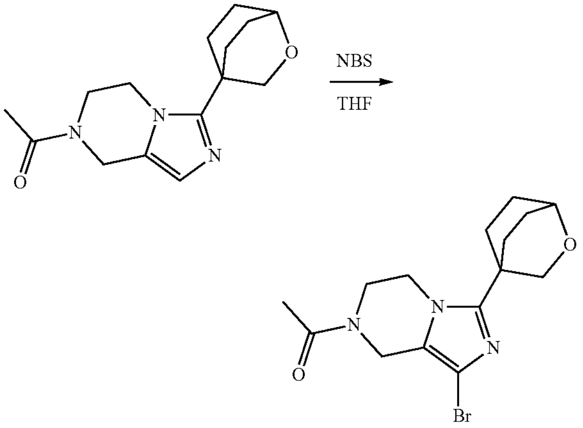

1-(3-(2-Oxabicyclo[2.2.2]octan-4-yl)-1-bromo-5,6-dihydroimidazo[1,5-α]pyrazin-7 (8H)-yl)ethanone.

To a mixture of the product from the previous step (1.50 g, 5.08 mmol) in THF (60 mL) was added NBS (904.95 mg, 5.08 mmol). The mixture was stirred at RT for 15 min, then poured into ice-water and extracted with $CH_2Cl_2$ (75 mL×3). The combined organic layers were dried over $MgSO_4$, filtered and concentrated under reduced pressure. The residue was purified by $SiO_2$ gel chromatography (0% to 10% MEOH in $CH_2Cl_2$) to give the title compound as a white solid (1.16 g, 64%). MS ($ES^+$): $C_{15}H_{20}BrN_3O_2$ requires: 353, found: 354 $[M+H]^+$.

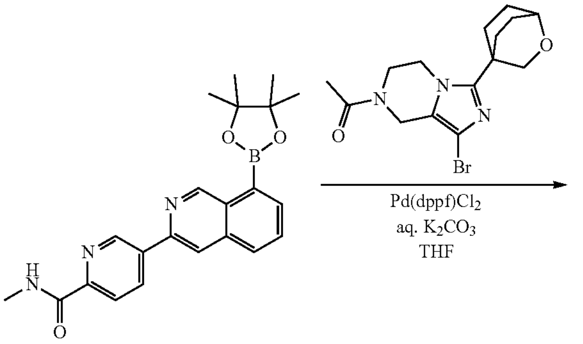

-continued

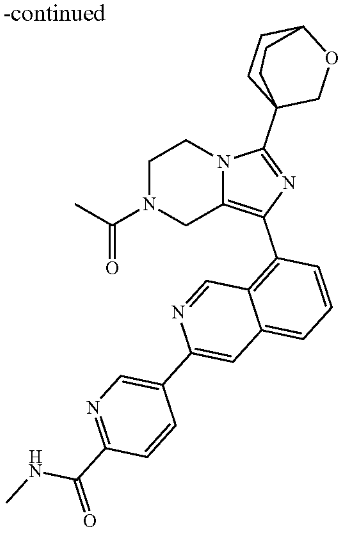

5-(8-(7-Acetyl-3-(2-oxabicyclo[2.2.2]octan-4-yl)-5,6,7,8-tetrahydroimidazo[1,5-α]pyrazin-1-yl)isoquinolin-3-yl)-N-methylpicolinamide A mixture of Intermediate "C" (1.65 g, 4.25 mmol), the product from the previous step (1.16 g, 3.27 mmol) and Pd (dppf) $Cl_2$ (272.40 mg, 326.89 μmoles) in THF (75 mL) was degassed by purging with $N_2$ then treated with 2.0 M aq. $K_2CO_3$ (4.9 mL, 9.8 mmoles) injected by syringe. The mixture was purged with $N_2$ 3 times, then stirred under $N_2$ at 90° C. overnight. The mixture was concentrated, and the residue was and purified by $SiO_2$ gel chromatography (0% to 75% (10% MeOH in EtOAc) in $CH_2Cl_2$) to give the title compound as a pale yellow solid (1.29 g, 73%).

MS ($ES^+$): $C_{31}H_{32}N_6O_3$ requires: 536, found: 537 $[M+H]^+$.

$^1H$ NMR (400 MHz, $CDCl_3$) (ca. 1:1 mixture of rotamers) δ 9.85 (appar d, J=10.7 Hz, 1H), 9.28 (appar d, J=5.4 Hz, 1H), 8.57 (appar d, J=8.1 Hz, 1H), 8.32 (appar d, J=8.1 Hz, 1H), 8.15 (appar d, J=9.2 Hz, 1H), 8.14-8.10 (m, 1H), 7.89-7.84 (m, 1H), 7.77-7.73 (m, 1H), 7.51-7.47 (m, 1H), 4.84 (s, 1H), 4.75 (s, 1H), 4.43-4.21 (m, 4H), 4.09-3.83 (m, 3H), 3.08 (d, J=5.1 Hz, 3H), 2.33-2.20 (m, 6H), 2.20 (s, 1.5H), 2.09 (s, 1.5H) 1.89-1.72 (m, 2H).

Example 5

5-(8-(7-Acetyl-3-(tetrahydro-2H-pyran-4-yl)-5,6,7,8-tetrahydroimidazo[1,5-α]pyrazin-1-yl)-7-fluoroisoquinolin-3-yl)-N-methylpicolinamide

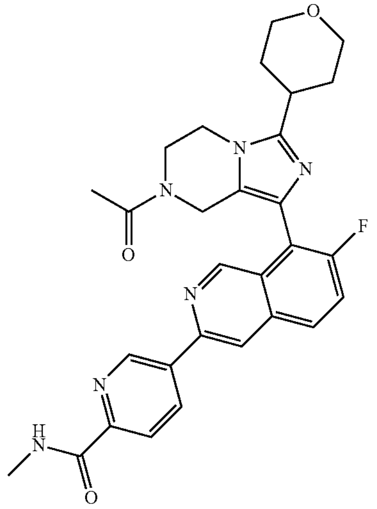 [SMILES: CNC(=O)c1ccc(-c2cc3ccc(F)c(-c4nc(C5CCOCC5)n5c4CN(C(C)=O)CC5)c3cn2)cn1]

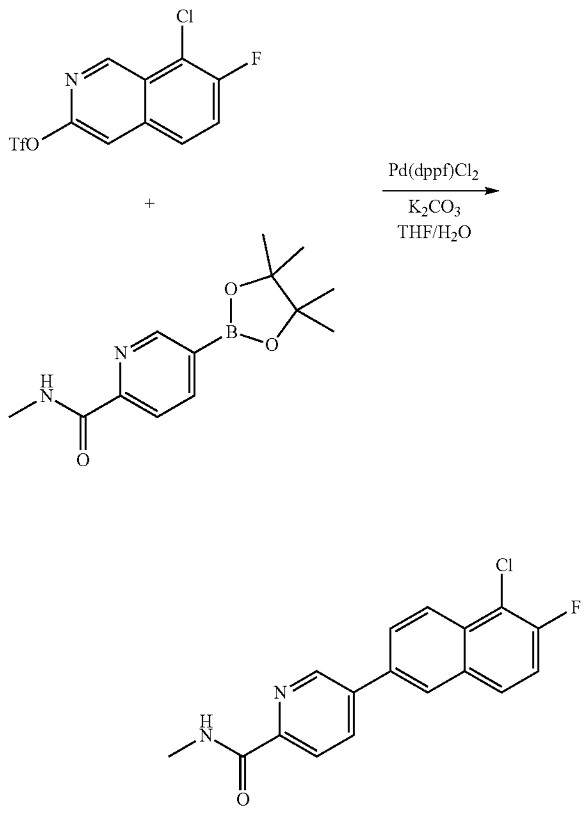

5-(8-Chloro-7-fluoroisoquinolin-3-yl)-N-methylpicolinamide

To a degassed solution of Intermediate "D" (1.00 g, 3.04 mmol) in 4:1 THF/water (50 mL) were added N-methyl-5-(4,4,5,5-tetramethyl-1,3,2-dioxaborolan-2-yl)picolinamide (0.797 g, 3.04 mmol), $K_2CO_3$ (839 mg, 6.08 mmol), and Pd(dppf)$Cl_2$ (244 mg, 0.333 mmol). The resulting mixture was stirred at 100° C. for 6 h, then concentrated under reduced pressure. The residue was slurried in water (20 mL) and solid was isolated by filtration to give the title compound as a gray solid (0.7 g, 73%). MS ($ES^+$) $C_{16}H_{11}ClFN_3O$ requires: 315, found: 316 $[M+H]^+$.

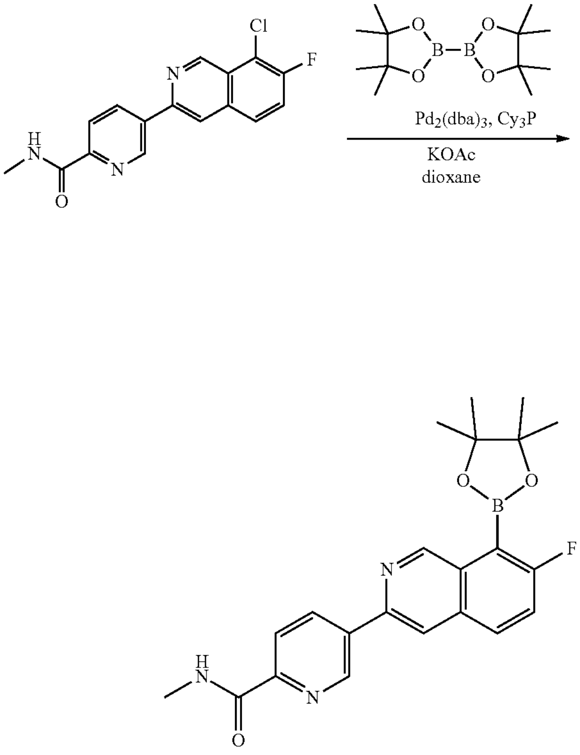

5-(7-Fluoro-8-(4,4,5,5-tetramethyl-1,3,2-dioxaborolan-2-yl)isoquinolin-3-yl)-N-methylpicolinamide To a degassed solution of the product from the previous step (60 mg, 0.19 mmol) in dioxane (3 ml) was added $B_2Pin_2$ (720 mg, 0.285 mmol), KOAc (37 mg, 0.38 mmol), tricyclohexylphosphine (5.3 mg, 0.019 mmol) and $Pd_2(dba)_3$ (17 mg, 0.019 mmol). The resulting mixture was stirred at 110° C. under argon for 16 h in a sealed tube, then concentrated under reduced pressure to give crude title compound, which was directly used in the next step. MS ($ES^+$) $C_{22}H_{23}BFN_3O_3$ requires: 407, found: 408 $[M+H]^+$.

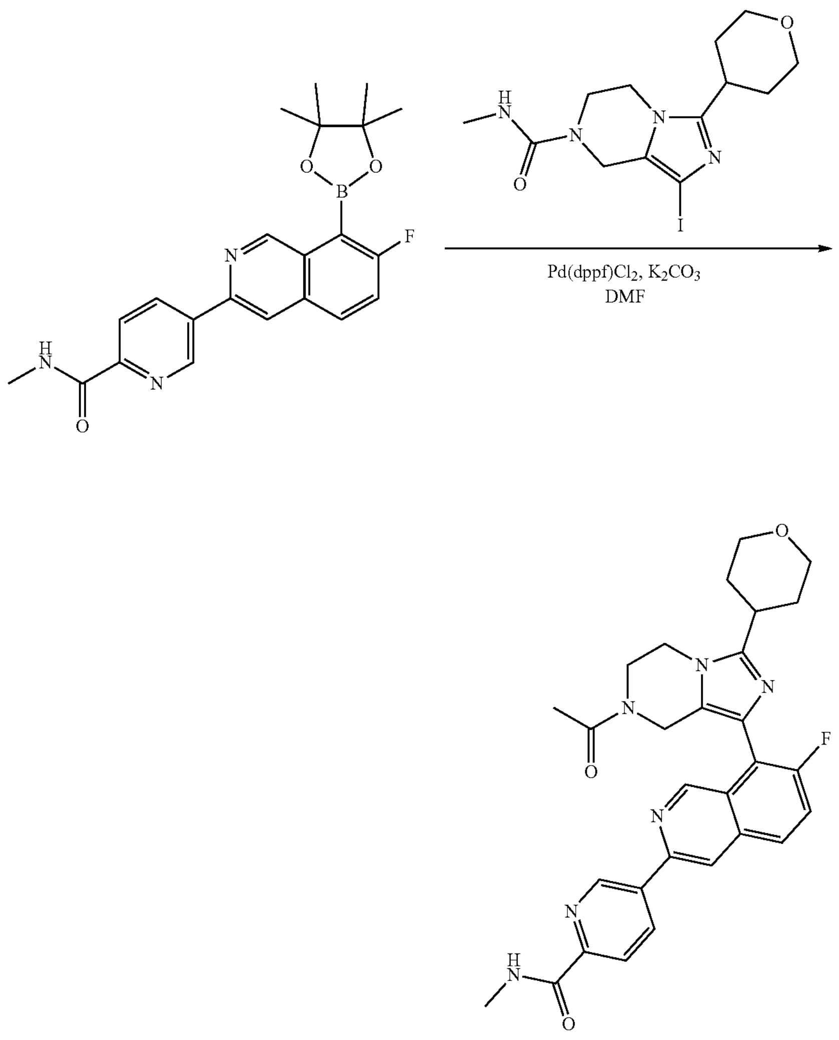

tert-Butyl 5-(8-(7-acetyl-3-(tetrahydro-2H-pyran-4-yl)-5,6,7,8-tetrahydroimidazo[1,5-α]pyrazin-1-yl)-7-fluoroisoquinolin-3-yl)-N-methylpicolinamide To a degassed solution of Intermediate "B" (assumed 0.19 mmol) in 4:1 dioxane/water (10 mL) was added the product from the previous step (76 mg, 0.19 mmol), $K_2CO_3$ (50 mg, 0.36 mmol), Pd (dppf) $Cl_2$ (14 mg, 0.018 mmol). The resulting mixture was stirred at 100° C. for 2 h, then concentrated under reduced pressure. The residue was purified by reverse phase preparative HPLC (Mobile phase: A=0.1% $NH_4HCO_3/H_2O$, B=MeCN; Gradient: B=25% to 65% in 12 min; Column: C18) to give the title compound as a white solid (7.5 mg, 7%).

MS ($ES^+$) $C_{29}H_{29}FN_6O_3$ requires: 528, found: 529 $[M+H]^+$.

$^1H$ NMR (500 MHZ, $CD_3OD$) (ca. 2:1 mixture of rotamers) δ 9.82 (s, 0.7H), 9.75 (s, 0.3H), 9.30-9.28 (m, 1H), 8.66 (appar d, J=8.1 Hz, 1H), 8.50 (appar d, J=8.2 Hz, 1H), 8.23-8.15 (m, 2H), 7.79-7.73 (m, 1H), 4.76 (s, 0.7H), 4.71 (s, 1.3H), 4.34 (t, J=6.0 Hz, 1.3H), 4.25 (t, J=5.5 Hz, 0.7H), 4.10-4.06 (m, 4H), 3.65 (t, J=12.0 Hz, 2H), 3.27-3.23 (m, 1H), 3.02 (s, 3H), 2.25 (s, 2H), 2.14 (s, 1H), 2.09-1.96 (m, 4H).

Example 6

1-(1-(7-fluoro-3-(2-methylthiazol-5-yl)isoquinolin-8-yl)-3-(tetrahydro-2H-pyran-4-yl)-5,6-dihydroimidazo[1,5-α]pyrazin-7 (8H)-yl)ethan-1-one

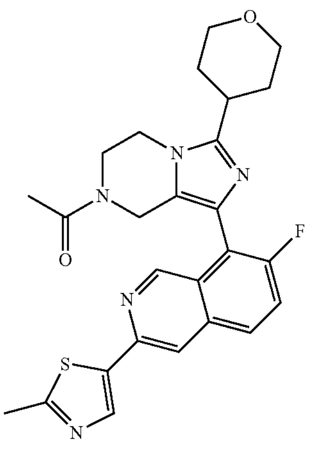 [SMILES: CC(=O)N1CCn2c(C3CCOCC3)nc(-c3c(F)ccc4cc(-c5cnc(C)s5)ncc34)c2C1]

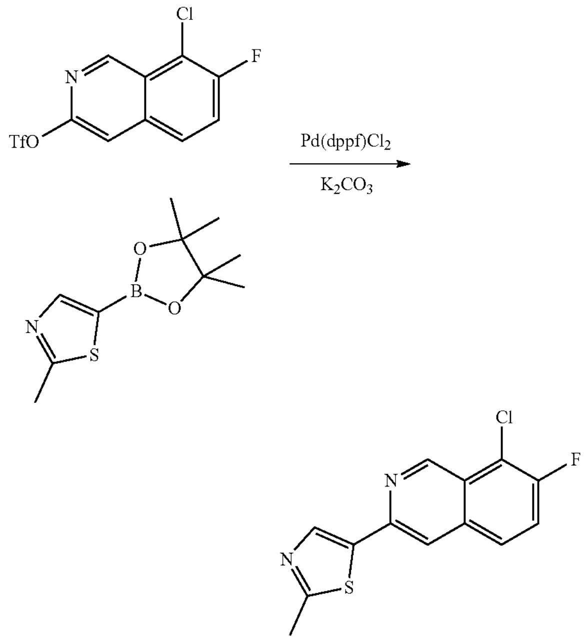

5-(8-Chloro-7-fluoroisoquinolin-3-yl)-2-methylthiazole.

A mixture of Intermediate "D" (500 mg, 1.52 mmol), 2-methyl-5-(4,4,5,5-tetramethyl-1,3,2-dioxaborolan-2-yl) thiazole (412 mg, 1.83 mmol), Pd (dppf) $Cl_2$ (110 mg, 0.15 mmol), and $K_2CO_3$ (630 mg, 4.56 mmol) in dioxane (15 mL) and $H_2O$ (3 mL) was stirred at 80° C. for 2 h. The mixture was poured into water (40 mL) and extracted with EtOAc (40 mL×3). The combined organic layers were dried over $Na_2SO_4$, filtered and concentrated under reduced pressure. The residue was purified by $SiO_2$ gel chromatography (70% to 100% EtOAc in petroleum ether) to give the title compound as a gray solid (460 mg, 100%). MS ($ES^+$) $C_{13}H_8ClFN_2S$ requires: 278, found: 279 $[M+H]^+$.

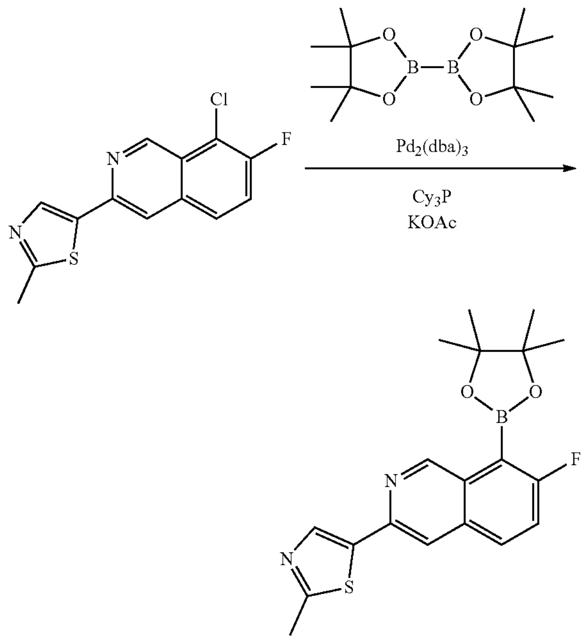

5-(7-Fluoro-8-(4,4,5,5-tetramethyl-1,3,2-dioxaborolan-2-yl)isoquinolin-3-yl)-2-methylthiazole.

A mixture of the product from the previous step (70 mg, 0.25 mmol) and $Pd_2$ (dba) 3 (28 mg, 0.03 mmol), $Cy_3P$ (23 mg, 0.08 mmol), KOAc (106 mg, 1.08 mmol) and $B_2Pin_2$ (97 mg, 0.38 mmol) in dioxane (3 mL) was stirred at 120° C. overnight. The mixture was allowed to cool to RT, filtered, and the filtrate concentrated to give the crude title compound (63 mg, 68%), which was used without further purification. MS ($ES^+$) $C_{19}H_{20}BFN_2O_2S$ requires: 370, found: 371 $[M+H]^+$.

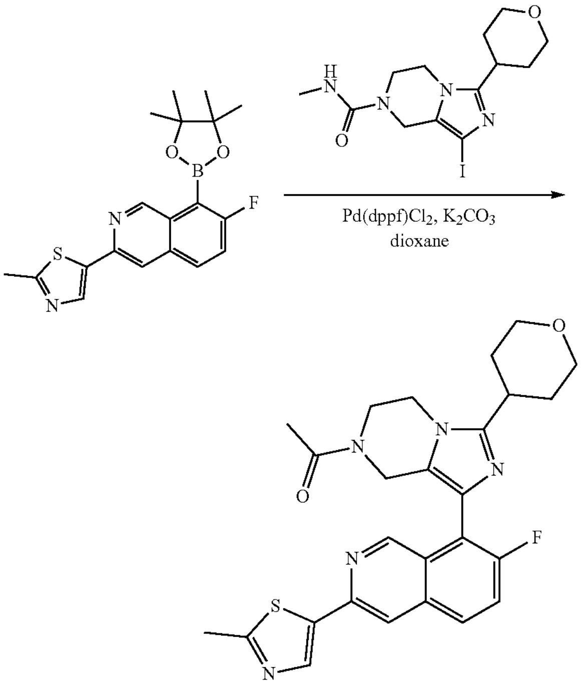

1-(1-(7-Fluoro-3-(2-methylthiazol-5-yl)isoquinolin-8-yl)-3-(tetrahydro-2H-pyran-4-yl)-5,6-dihydroimidazo[1,5-α] pyrazin-7 (8H)-yl)ethanone To a degassed solution of Intermediate "B" (70 mg, 0.18 mmol) in 4:1 dioxane/water (10 mL) were added 5-(7-fluoro-8-(4,4,5,5-tetramethyl-1,3,2-dioxaborolan-2-yl)isoquinolin-3-yl)-2-methylthiazole (68.8 mg, 0.186 mmol), $K_2CO_3$ (50 mg, 0.37 mmol), and Pd(dppf)$Cl_2$ (14 mg, 0.018 mmol). The resulting mixture was stirred at 100° C. for 2 h, then concentrated under reduced pressure. The residue was purified by reverse phase preparative HPLC (Mobile phase: A=0.1% $NH_4HCO_3/H_2O$, B=MeCN; Gradient: B=30% to 85% in 11 min; Column: C18) to give the title compound as a white solid (13.5 mg, 15%).

MS ($ES^+$) $C_{26}H_{26}FN_5O_2S$ requires: 491, found: 492 $[M+H]^+$.

$^1H$ NMR (500 MHZ, $CDCl_3$) (ca. 2:1 mixture of rotamers) δ 9.62 (s, 0.7H), 9.56 (s, 0.3H), 8.18 (s, 1H), 7.92-7.91 (m, 1H), 7.84-7.81 (m, 1H), 7.52 (appar t, J=9.4 Hz, 1H), 4.74 (s, 0.7H), 4.65 (s, 1.3H), 4.33-3.96 (m, 6H), 3.56 (t, J=11.7 Hz, 2H), 3.02-2.83 (m, 1H), 2.77 (s, 3H), 2.27-2.01 (m, 5H), 1.90-1.88 (m, 2H).

The activity of the compounds in Examples 1-6 as inhibitors of CBP and BRD4 is illustrated in the following assays. The other compounds listed above, which have not yet been made and/or tested, are predicted to have activity in these assays as well.

Biological Activity Assays

Specific binding of the CBP or BRD4 bromodomain to the acetylated peptide derived from the H4 histone substrate (tetra acetylated H4 (1-21) Ac—K5/8/12/16) was measured in absence or presence of inhibitors. The GST tagged bromodomains of CBP (1081-1197) and BRD4 (49-170) were obtained from BPS Bioscience and binding to the biotinylated H4 (1-21) Ac—K5/8/12/16 (AnaSpec. 64989) was assessed via AlphaScreen technology (Perkin Elmer).

CBP AlphaScreen assay: 5 nM GST-CBP (1081-1197) and 20 nM biotin-H4 (1-21) Ac—K5/8/12/16 (AnaSpec. 64989) were incubated with varying concentrations of CBP inhibitors in 15 μL of buffer containing 50 mM HEPES 7.5, 100 nM NaCl, 1 mM TCEP, and 0.003% Tween-20. After 30 minutes incubation at room temperature, 15 μL of detection buffer (BPS Bio. 33006) containing 7 μg/mL of Glutathione AlphaLisa acceptor beads (Perkin Elmer AL109) and 14 μg/mL of Streptavidin donor beads (Perkin Elmer 676002) was then added to the previous mixture. The reaction was incubated for an additional 2 hours at room temperature, and the AlphaScreen signal was quantified using the Envision Multilabel plate reader. As negative control, GST-CBP (1081-1197) was incubated with the non-acetylated biotin-H4 (1-21) peptide (AnaSpec. 62555) and in presence of 0.25% of final DMSO concentration.

BRD4 AlphaScreen assay: The binding of 2.5 nM of BRD4 (49-170) to 10 nM biotin-H4 (1-21) Ac—K5/8/12/16 (AnaSpec. 64989) was assessed following the same procedure described for the CBP assay. The standard dose response curves were fitted by Genedata Screener software using the variable-slope model:

$$Signal=Signal_{negative\ control}+(Signal_{DMSO\ control}-Signal_{negative\ control})/(1+(IC_{50}/Dose)/\backslash Hill\ slope).$$

Only Signal and Dose in the equation were treated as known values.

Results are given below in Table 1, which shows that the instant compounds inhibit CBP and are selective over BRD4. Structural analogs Compounds 7 and 8 were previously disclosed in U.S. Patent Publication No. 2019/0298729 (U.S. application Ser. No. 16/370,404), which is incorporated herein in its entirety.

TABLE 1

| Biological Activity | | |
|---|---|---|
| Compound | CBP $IC_{50}$ (nM) | BRD4 $IC_{50}$ (nM) |
| 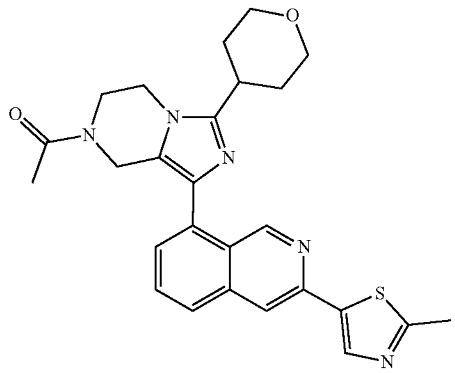 [SMILES: CC(=O)N1CCn2c(C3CCOCC3)nc(-c3cccc4cc(-c5cnc(C)s5)ncc34)c2C1] Compound 1 | 7 | 13174 |
| 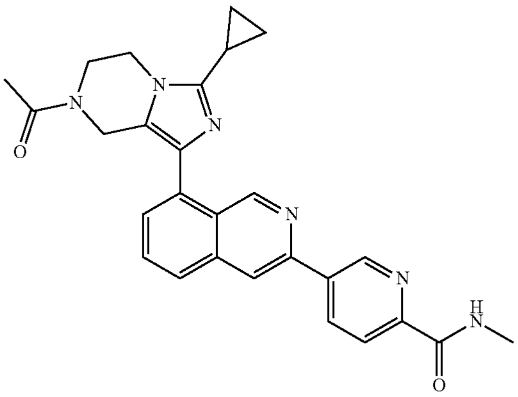 [SMILES: CNC(=O)c1ccc(-c2cc3cccc(-c4nc(C5CC5)n5c4CN(C(C)=O)CC5)c3cn2)cn1] Compound 2 | 15 | 25000 |

TABLE 1-continued
| Biological Activity | | |
|---|---|---|
| Compound | CBP $IC_{50}$ (nM) | BRD4 $IC_{50}$ (nM) |
| 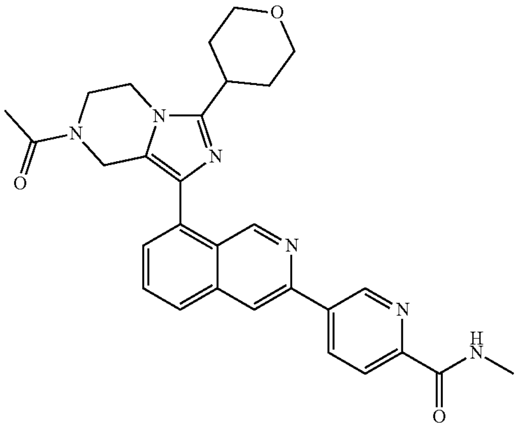 [SMILES: CNC(=O)c1ccc(-c2cc3cccc(-c4nc(C5CCOCC5)n5c4CN(C(C)=O)CC5)c3cn2)cn1] Compound 3 | 16 | 14970 |
| 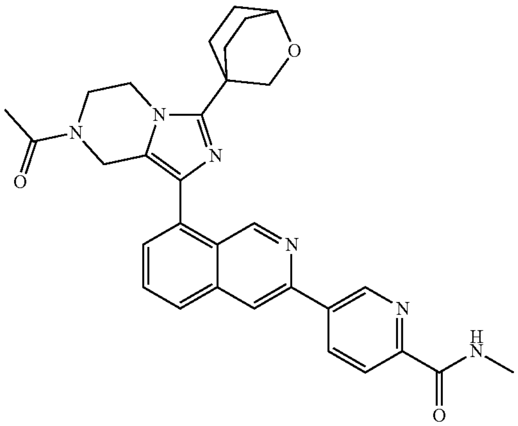 [SMILES: CNC(=O)c1ccc(-c2cc3cccc(-c4nc(C56CCC(CC5)OC6)n5c4CN(C(C)=O)CC5)c3cn2)cn1] Compound 4 | 22 | 17029 |
| 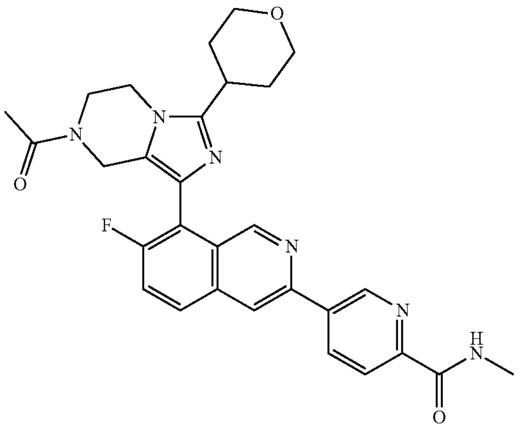 [SMILES: CNC(=O)c1ccc(-c2cc3ccc(F)c(-c4nc(C5CCOCC5)n5c4CN(C(C)=O)CC5)c3cn2)cn1] Compound 5 | 34 | 20394 |

TABLE 1-continued
| Biological Activity | | |
|---|---|---|
| Compound | CBP $IC_{50}$ (nM) | BRD4 $IC_{50}$ (nM) |
| 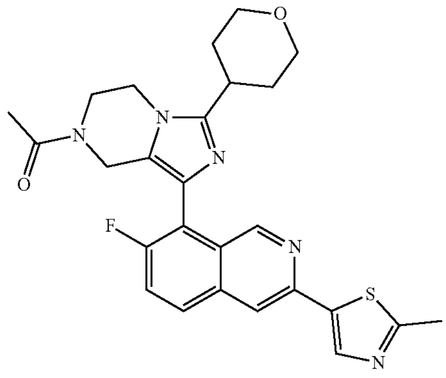 [SMILES: CC(=O)N1CCn2c(C3CCOCC3)nc(-c3c(F)ccc4cc(-c5cnc(C)s5)ncc34)c2C1] Compound 6 | 14 | 22222 |
| 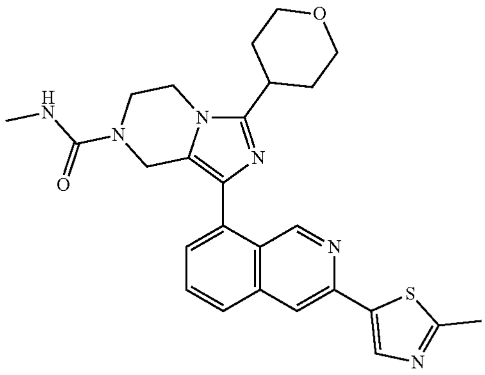 Compound 7 | 1 | 3475 |
| 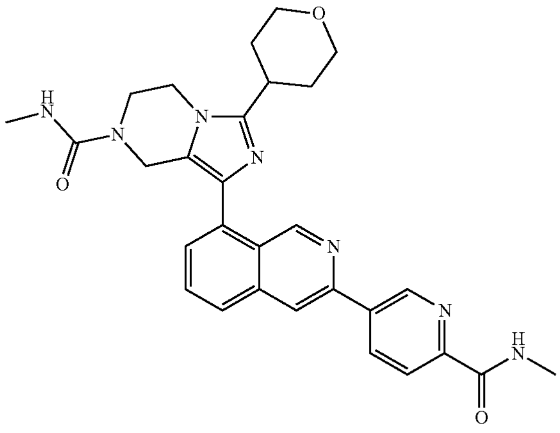 Compound 8 | 1 | 5967 |

DOHH2 Proliferation Assay: On day 1, 1000 DOHH2 cells were seeded to a 384-well TC plate (PerkinElmer #6007680) in 40 μL RPMI 1640 media, followed by the addition of CBP inhibitors except for column 13 where 3.3 μM staurosporine was added as negative control. DMSO was 0.1% in all the wells. The cells were lysed in and counted viability by 40 μL CellTiter-Glo (Promega #G9243) on day 7. The luminescent signal was quantified by Envision Multilabel plate reader and the standard dose response curves were fitted by Genedata Screener software using the variable-slope model:

$$Signal=Signal_{negative\ control}+(Signal_{DMSO\ control}-Signal_{negative\ control})/(1+(IC_{50}/Dose)/\backslash Hill\ slope).$$

Only Signal and Dose in the equation were treated as known values.

Results of the assay are shown below.

TABLE 2

| Biological Activity | |
|---|---|
| Compound | DOHH2 $IC_{50}$ (nM) |
| 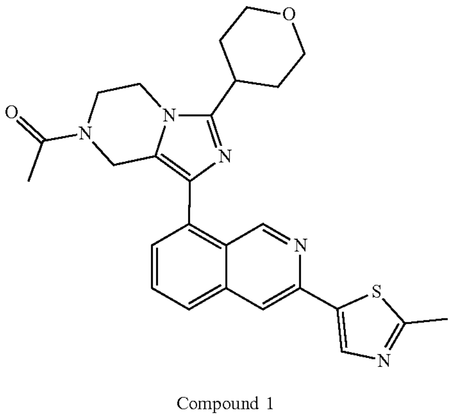 Compound 1 | 261 |
| 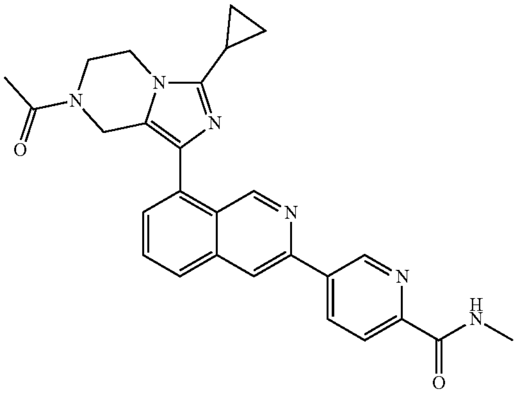 [SMILES: CNC(=O)c1ccc(-c2cc3cccc(-c4nc(C5CC5)n5c4CN(C(C)=O)CC5)c3cn2)cn1] Compound 2 | 376 |
| 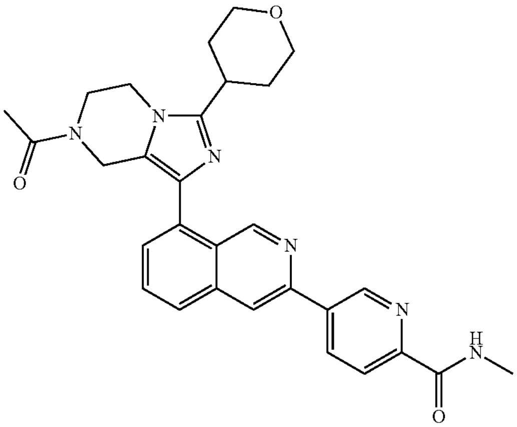 [SMILES: CNC(=O)c1ccc(-c2cc3cccc(-c4nc(C5CCOCC5)n5c4CN(C(C)=O)CC5)c3cn2)cn1] Compound 3 | 232 |

TABLE 2-continued
| Biological Activity | |
|---|---|
| Compound | DOHH2 $IC_{50}$ (nM) |
| 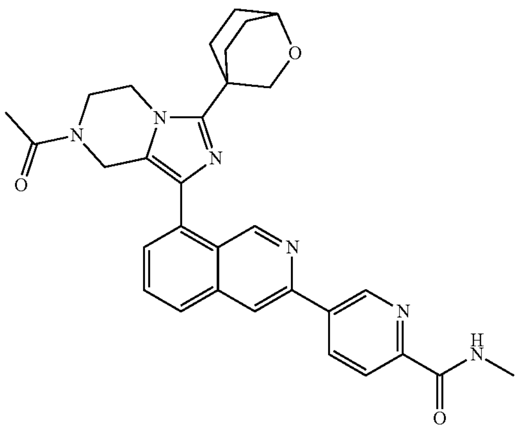 [SMILES: CNC(=O)c1ccc(-c2cc3cccc(-c4nc(C56CCC(CC5)OC6)n5c4CN(C(C)=O)CC5)c3cn2)cn1]<br>Compound 4 | 676 |
| 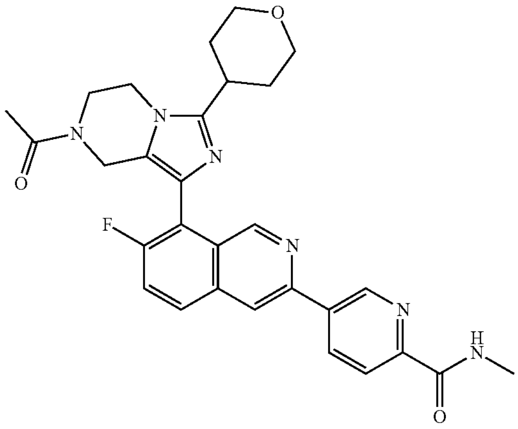 [SMILES: CNC(=O)c1ccc(-c2cc3ccc(F)c(-c4nc(C5CCOCC5)n5c4CN(C(C)=O)CC5)c3cn2)cn1]<br>Compound 5 | 216 |
| 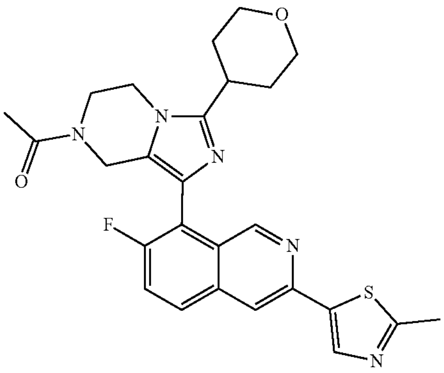 [SMILES: CC(=O)N1CCn2c(C3CCOCC3)nc(-c3c(F)ccc4cc(-c5cnc(C)s5)ncc34)c2C1]<br>Compound 6 | 541 |

TABLE 2-continued

| Biological Activity | |
|---|---|
| Compound | DOHH2 $IC_{50}$ (nM) |
| 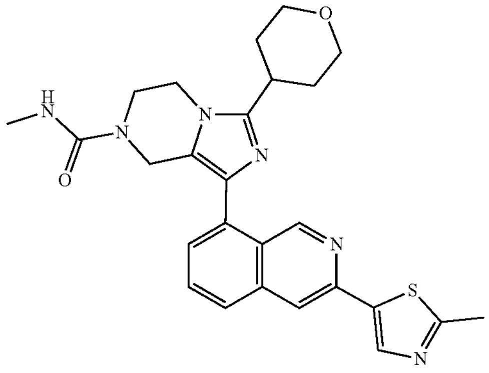 Compound 7 | 134 |

The compounds described herein show unexpected improvements in in vivo pharmacokinetics, specifically clearances and half-lives in mouse as an in vivo model used for screening pharmacokinetic behaviour, not predicted by in vitro microsomal stability data and not for obvious reasons based on structure. Relevant comparative data are shown in Tables 3 and 4. Table 3 shows that in vitro microsomal stabilities are similar or lower for Compounds 1 and 3 when compared to the structural analogs previously disclosed. However, as shown in Table 4, there is a dramatic decrease in mouse in vivo clearances and increase in half-lives for Compounds 1 and 3 compared to the structural analogs previously disclosed.

TABLE 3

| Metabolic Stability in Liver Microsome Preparations | | | |
|---|---|---|---|
| | Half-life in liver microsomes ($t_{1/2}$, minutes) | | |
| Compound | Mouse | Rat | Human |
| 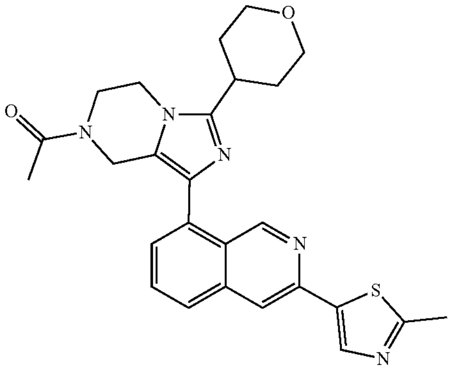 [SMILES: CC(=O)N1CCn2c(C3CCOCC3)nc(-c3cccc4cc(-c5cnc(C)s5)ncc34)c2C1] Compound 1 | 393 | 1225 | 310 |

TABLE 3-continued

Metabolic Stability in Liver Microsome Preparations

| Compound | Half-life in liver microsomes ($t_{1/2}$, minutes) | | |
|---|---|---|---|
| | Mouse | Rat | Human |
| 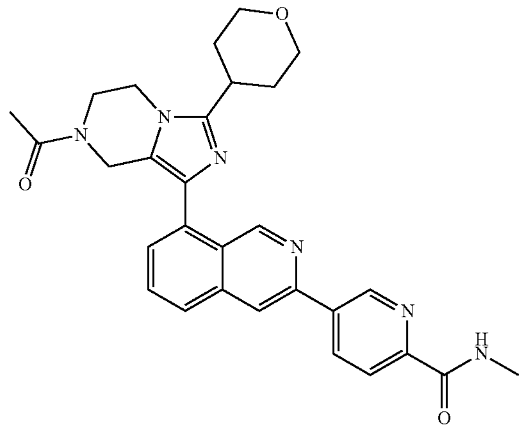 [SMILES: CNC(=O)c1ccc(-c2cc3cccc(-c4nc(C5CCOCC5)n5c4CN(C(C)=O)CC5)c3cn2)cn1] Compound 3 | 482 | 302 | 289 |
| 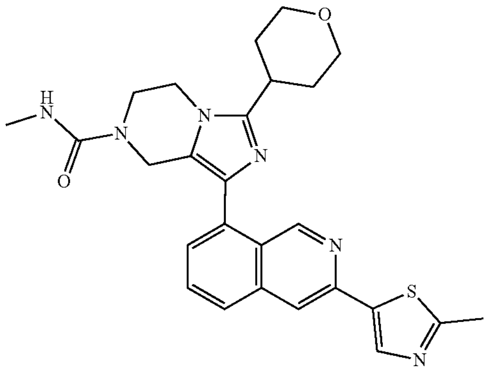 Compound 7 | 5199 | 507 | 261 |
| 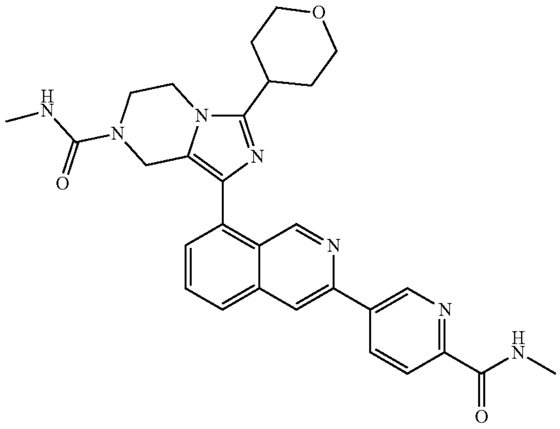 Compound 8 | 610 | 540 | 462 |

Method:

Test compound was incubated with liver microsomes (0.5 mg/mL) from CD-1 mouse, Sprague Dawley rat, and human in the presence of NADPH for 45 minutes at 37° C. The % parent remaining over time was determined by LC-MS/MS, using peak area ratios. Half-life ($t_{1/2}$) was calculated using the following equation: $t_{1/2} = \ln 2/k$, where k is the rate constant of parent decay over time (slope of the plot of log[% parent remaining] versus time).

TABLE 4
| In Vivo Pharmacokinetics After a Single Dose—Female CD-1 Mice | | | |
|---|---|---|---|
| Compound | Clearance (L/h/kg) | $V_{ss}$ (L/kg) | $t_{1/2}$ (h) |
| 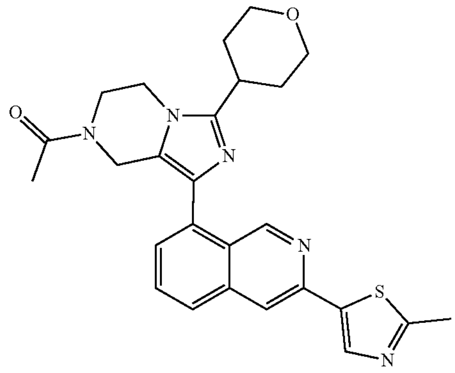 [SMILES: CC(=O)N1CCn2c(C3CCOCC3)nc(-c3cccc4cc(-c5cnc(C)s5)ncc34)c2C1] Compound 1 | 0.372 | 1.45 | 2.99 |
| 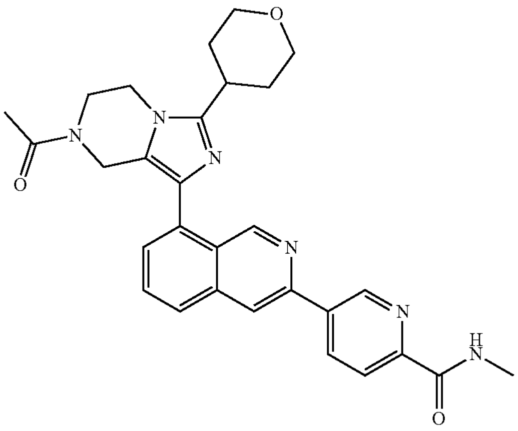 [SMILES: CNC(=O)c1ccc(-c2cc3cccc(-c4nc(C5CCOCC5)n5c4CN(C(C)=O)CC5)c3cn2)cn1] Compound 3 | 0.713 | 1.84 | 2.55 |
| 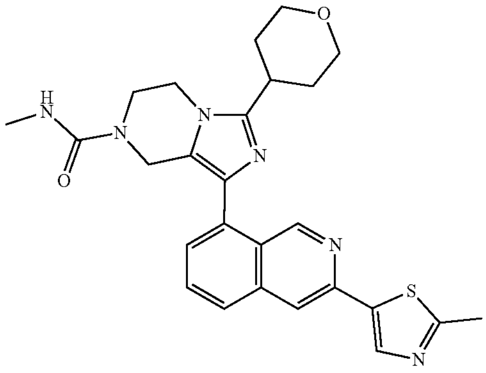 Compound 7 | 2.01 | 0.822 | 0.318 |

TABLE 4-continued

| In Vivo Pharmacokinetics After a Single Dose—Female CD-1 Mice | | | |
|---|---|---|---|
| Compound | Clearance (L/h/kg) | $V_{ss}$ (L/kg) | $t_{1/2}$ (h) |
| 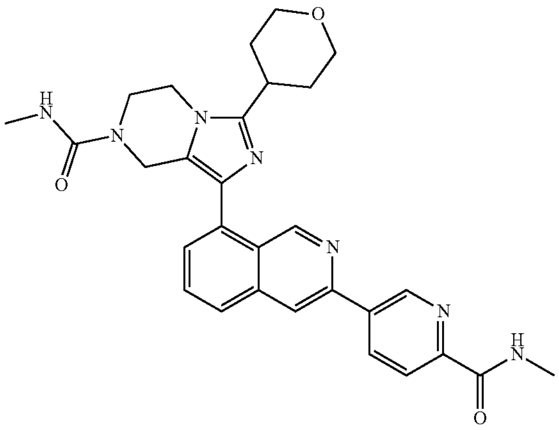 Compound 8 | 3.29 | 2.00 | 0.588 |

0.2 or 0.3 mg/kg IV (intravenous) dosing.

Compound 1 was further characterized for in vivo pharmacokinetics in rat, monkey and dog. Table 5 shows microsomal stabilities for Compound 1 in those species not already shown in Table 3. Table 6 shows pharmacokinetic parameters in rat, monkey and dog after single doses, intravenous (IV) and per os (PO).

TABLE 5

| Metabolic Stability of Compound 1 in Monkey and Dog Liver Microsome Preparations | | |
|---|---|---|
| | Liver microsomal clearance ($t_{1/2}$, minutes) | |
| Compound | Monkey | Dog |
| 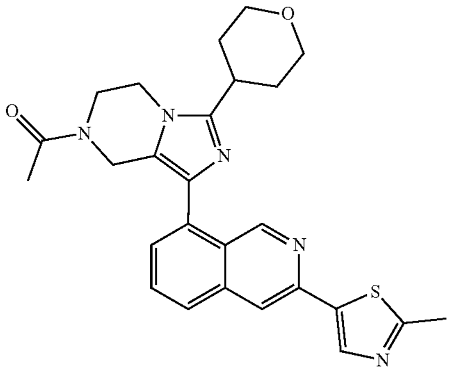 [SMILES: CC(=O)N1CCn2c(C3CCOCC3)nc(-c3cccc4cc(-c5cnc(C)s5)ncc34)c2C1] Compound 1 | 97 | 713 |

TABLE 6

| In Vivo Pharmacokinetics in Rat, Monkey and Dog After a Single Dose of Compound 1 | | | |
|---|---|---|---|
| PK Parameters | Sprague-Dawley Rat | Cynomolgus Monkey | Beagle Dog |
| Clearance (L/h/kg) | 0.673 | 0.418 | 0.258 |
| $V_{ss}$ (L/kg) | 2.31 | 2.28 | 3.38 |

TABLE 6-continued

| In Vivo Pharmacokinetics in Rat, Monkey and Dog After a Single Dose of Compound 1 | | | |
|---|---|---|---|
| PK Parameters | Sprague-Dawley Rat | Cynomolgus Monkey | Beagle Dog |
| $t_{1/2}$ (h) | 3.82 | 4.74 | 9.74 |
| $C_{max}$ (μM) | 23.0 | 1.97 | 2.56 |

TABLE 6-continued

In Vivo Pharmacokinetics in Rat, Monkey and Dog After a Single Dose of Compound 1

| PK Parameters | Sprague-Dawley Rat | Cynomolgus Monkey | Beagle Dog |
|---|---|---|---|
| $AUC_{last}$ (h * μM) | 124 | 11.3 | 26.2 |
| % F | 129 | 70.5 | 119 |

Doses were 1 mg/kg IV (intravenous) and 3 mg/kg PO (per os), except for the rat PO dose (30 mg/kg). Clearance, $Vd_{ss}$ and $t_{1/2}$ were determined from the IV dose and $C_{max}$, $AUC_{last}$ and F % were determined from the PO dose.

Microsomal stability. Microsomal stability assays were conducted on a Beckmann Biomek FXp laboratory automation system. The liver microsomal incubation mixture consisted of liver microsomes (0.5 mg microsomal protein/mL), the Compound (1 μM), $MgCl_2$ (3 mM), and EDTA (1 mM) in potassium phosphate buffer (100 mM, pH 7.4). Midazolam and Ketanserin were used as the assay control substrates. The reaction was initiated with the addition of an NADPH regeneration solution (1.3 mM NADPH) and maintained at 37° C. with shaking. At five time points ranging from 0 to 45 min, aliquots (50 μL) were removed and quenched with acetonitrile (100 μL) containing an internal standard (imipramine). After vortex and centrifugation, samples were analyzed by LC-MS/MS. Calculation of the in vitro half-lives and clearance followed literature guidelines. In Vivo Pharmacokinetics.

IV (intravenous) doses were formulated in 20% DMSO+60% PEG400+20% water. PO (per os) doses were formulated in 0.5% methylcellulose in water.

Mouse: Female mice (CD1 strain, purchased from Shanghai JH Laboratory Animal Co. LTD) weighing 20-30 g were used for studies. Food and water were available to all animals ad libitum. The test article was dosed via tail vein (IV doses) or oral gavage (PO doses), respectively. Blood samples were collected from all animals at predose and at 0.083, 0.25, 0.5, 1, 2, 4, 8, and 24 h postdose into tubes containing the anticoagulant K2EDTA (3 animals per time point with 3 time points collected per animal). Plasma was separated from the blood by centrifugation at 4° C. and stored at −70° C. until analysis. Test article concentrations in plasma were quantified using a liquid chromatography with tandem mass spectrometry (LC-MS/MS) method.

Rat: Male rats (SD strain, purchased from Shanghai JH Laboratory Animal Co. LTD) weighing 200-300 g were used for studies. Animals were fasted overnight and fed 4 h postdose. Water was available ad libitum for all animals. Test article was dosed via dorsal foot vein (IV doses) or oral gavage (PO doses). Blood samples were collected via tail vein from all animals at predose and at 0.083, 0.25, 0.5, 1, 2, 4, 8, and 24 h postdose into tubes containing the anticoagulant K2EDTA. Plasma was separated from the blood by centrifugation at 4° C. and stored at −70° C. until analysis. Test article concentrations in plasma were quantified using a liquid chromatography with tandem mass spectrometry (LC-MS/MS) method.

Dog: Male Beagle dogs (purchased from Beijing Marshall Biotechnology Co., Ltd) weighing 7-10 kg were used for studies. Animals were fasted overnight and fed 4 h postdose. Test article was administered to dogs via the cephalic vein (IV doses) or oral gavage (PO doses). Blood samples were collected via the saphenous vein or cephalic vein from all animals at predose and 0.083, 0.25, 0.5, 1, 2, 4, 8, and 24 h postdose into tubes containing the anticoagulant K2EDTA. Plasma was separated from the blood by centrifugation at 4° C. and stored at −70° C. until analysis. Test article concentrations in plasma were quantified using a liquid chromatography with tandem mass spectrometry (LC-MS/MS) method.

Monkey: Male Cynomolgus monkeys (purchased from Hainan Jingang Biotech. Co., Ltd) weighing 3-5 kg were used for studies. Animals were fasted overnight and fed 4 h postdose. Test article was administered to monkeys via the cephalic vein (IV doses) or nasal gavage (PO doses). Blood samples were collected via the saphenous vein or cephalic vein from all animals at predose and 0.083, 0.25, 0.5, 1, 2, 4, 8, and 24 h postdose into tubes containing the anticoagulant K2EDTA. Plasma was separated from the blood by centrifugation at 4° C. and stored at −70° C. until analysis. Test article concentrations in plasma were quantified using a liquid chromatography with tandem mass spectrometry (LC-MS/MS) method.

DOHH2 Xenograft study 4-6 weeks old CB17/scid female mice (Jackson Labs) were implanted with DOHH2 cells ($1\times10^6$ cells/mouse diluted with matrigel 1:1), which were injected subcutaneously on the right flank and allowed to grow to an average volume of 200-300 $mm^3$ as monitored by caliper measurements. At this point, animals were randomized into groups of 8 animals. All animals receive LabDict 5053 chow ad libitum. Animals were orally dosed with Example 1 (50 mg/kg. BID on a 5 days on/2 days off schedule) formulated in a vehicle of 0.5% methylcellulose in sterile water. Tumor volumes were measured twice a week by caliper and calculated using the formula: $V=I^2*L/2$ (1=length; L=width). Body weight was monitored for the duration of the studies. GraphPad Prism was used for generation of graphs, and data is expressed as the mean±standard error of the mean.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:

1. A compound having structural Formula I:

(I)

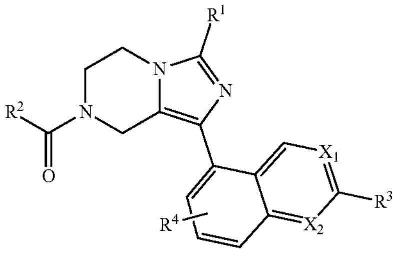

or a salt thereof, wherein:

$X_1$ is N and $X_2$ is CH;

$R^1$ is chosen from cyclopropyl, tetrahydro-2H-pyran-4-yl, and 2-oxabicyclo[2.2.2]octan-4-yl, any of which is optionally substituted with 1 or 2 $R^5$ groups;

$R^2$ is methyl;

$R^3$ is chosen from pyridin-3-yl and thiazol-5-yl, and is optionally substituted with 1 or 2 $R^7$ groups;

$R^4$ is chosen from H and fluoro;

each $R^5$ is independently chosen from alkyl, alkoxy, cyano, carboxy, halo, haloalkyl, haloalkoxyl, hydroxy, and oxo;

each occurrence of $R^7$ is independently chosen from —C(O)$NR^8R^9$ and alkyl, and $R^8$ and $R^9$ are independently chosen from hydrogen and alkyl.

2. The compound as recited in claim 1, or a salt thereof, wherein $R^1$ is chosen from cyclopropyl and tetrahydro-2H-pyran-4-yl.

3. The compound as recited in claim 1, or a salt thereof, wherein $R^3$ is chosen from 6-(methylcarbamoyl)pyridin-3-yl and 2-methylthiazol-5-yl.

4. The compound as recited in claim 1, having structural Formula I:

(I)

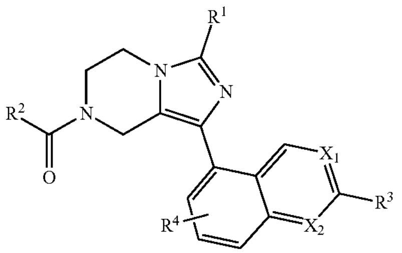

or a salt thereof, wherein:

$X_1$ is N and $X_2$ is CH;

$R^1$ is tetrahydro-2H-pyran-4-yl optionally substituted with 1 or 2 $R^5$ groups;

$R^2$ is methyl;

$R^3$ is thiazol-5-yl optionally substituted with 1 or 2 $R^7$ groups;

$R^4$ is chosen from H and fluoro;

each $R^5$ is independently chosen from alkyl, alkoxy, cyano, carboxy, halo, haloalkyl, haloalkoxyl, hydroxy, and oxo;

each occurrence of $R^7$ is independently chosen from —C(O)$NR^8R^9$ and alkyl, and $R^8$ and $R^9$ are independently chosen from hydrogen and alkyl.

5. The compound as recited in claim 4, or a salt thereof, wherein $R^1$ is tetrahydro-2H-pyran-4-yl.

6. The compound as recited in claim 4, or a salt thereof, wherein $R^7$ is alkyl.

7. The compound as recited in claim 6, or a salt thereof, wherein $R^7$ is methyl.

8. The compound as recited in claim 4, or a salt thereof, wherein $R^7$ is —C(O)$NHCH_3$.

9. The compound as recited in claim 1, having structural Formula II:

(II)

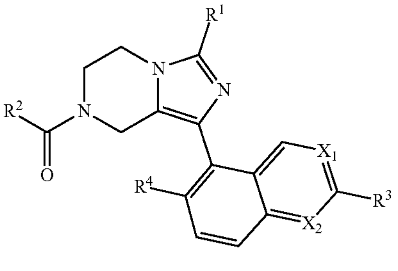

or a salt thereof, wherein:

$X_1$ is N and $X_2$ is CH;

$R^1$ is tetrahydro-2H-pyran-4-yl optionally substituted with 1 or 2 $R^5$ groups;

$R^2$ is methyl;

$R^3$ is chosen from pyridin-3-yl and thiazol-5-yl, and is optionally substituted with 1 or 2 $R^7$ groups;

$R^4$ is chosen from H or fluoro;

each $R^5$ is independently chosen from alkyl, alkoxy, cyano, carboxy, halo, haloalkyl, haloalkoxyl, hydroxy, and oxo;

each occurrence of $R^7$ is independently chosen from —C(O)$NR^8R^9$ and alkyl, and $R^8$ and $R^9$ are independently chosen from hydrogen and alkyl.

10. A pharmaceutical composition comprising a compound as recited in claim 1, or a salt thereof, together with a pharmaceutically acceptable carrier.

11. A method of treatment of a disease mediated by either one of CBP or P300 comprising the administration of a therapeutically effective amount of a compound as recited in claim 1, or a salt thereof, to a patient in need thereof.

12. The method as recited in claim 11, wherein said disease is chosen from a proliferative disease, an inflammatory disorder, an autoimmune disease, and a fibrotic disease.

13. The method as recited in claim 12, wherein said disease is a proliferative disease.

14. The method as recited in claim 13, wherein said disease is cancer.

15. The method as recited in claim 14, wherein said cancer is chosen from acoustic neuroma, acute leukemia, acute lymphocytic leukemia, acute myelocytic leukemia, acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer, and Wilms' tumor.

16. The method as recited in claim 15, wherein said cancer is chosen from lung cancer, breast cancer, pancreatic cancer, colorectal cancer, and melanoma.
17. The method as recited in claim 12, wherein said disease is an autoimmune disease.
18. The method as recited in claim 12, wherein said disease is a fibrotic disease.
19. A compound chosen from:
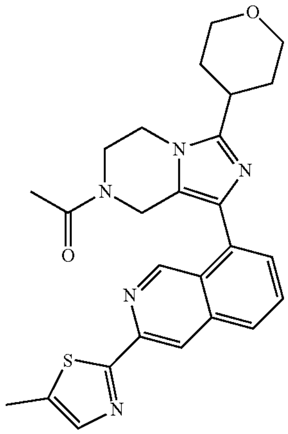
,
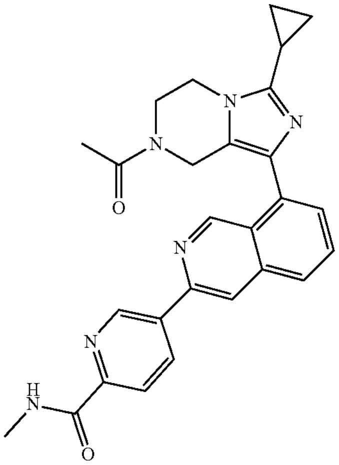
,
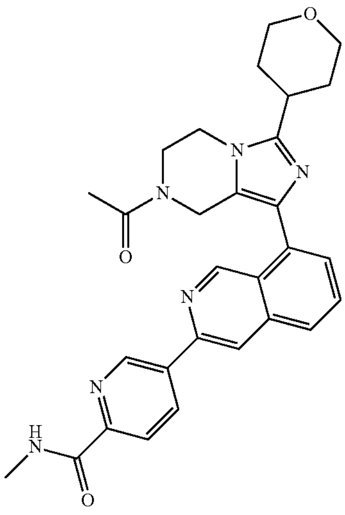
,
-continued
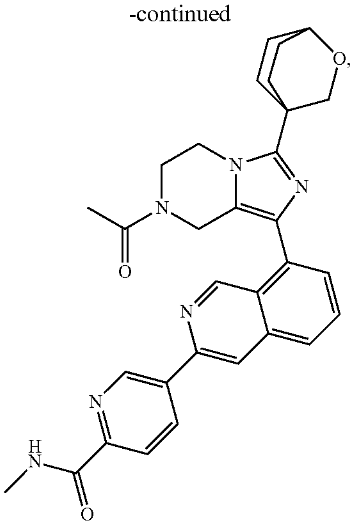
,
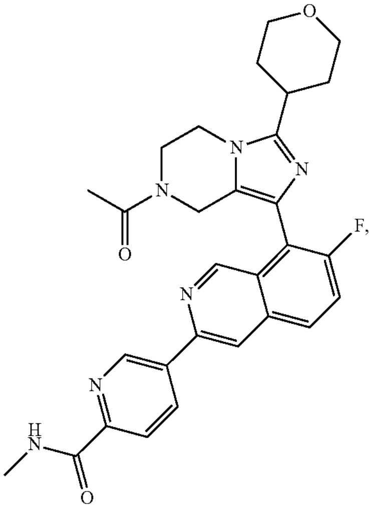
, and
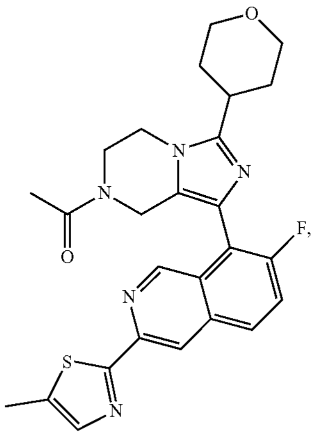
,
or a salt thereof.
* * * * *